US009642900B2

(12) United States Patent
Itoh et al.

(10) Patent No.: US 9,642,900 B2
(45) Date of Patent: May 9, 2017

(54) CTL INDUCER COMPOSITION

(71) Applicant: GREEN PEPTIDE CO., LTD., Fukuoka (JP)

(72) Inventors: Kyogo Itoh, Fukuoka (JP); Shigeki Shichijo, Fukuoka (JP); Akira Yamada, Fukuoka (JP)

(73) Assignee: GREEN PEPTIDE CO., LTD., Fukuoka (JP)

( * ) Notice: Subject to any disclaimer, the term of this patent is extended or adjusted under 35 U.S.C. 154(b) by 0 days.

(21) Appl. No.: 14/789,139

(22) Filed: Jul. 1, 2015

(65) Prior Publication Data
US 2015/0343041 A1 Dec. 3, 2015

Related U.S. Application Data

(62) Division of application No. 12/733,686, filed as application No. PCT/JP2008/066589 on Sep. 12, 2008, now Pat. No. 9,102,715.

(30) Foreign Application Priority Data

Sep. 18, 2007 (JP) ................. 2007-241161

(51) Int. Cl.
A61K 39/00 (2006.01)
C07K 14/005 (2006.01)
A61K 39/005 (2006.01)
C07K 7/06 (2006.01)
A61K 38/00 (2006.01)

(52) U.S. Cl.
CPC ........ A61K 39/0011 (2013.01); A61K 39/005 (2013.01); C07K 7/06 (2013.01); C07K 14/005 (2013.01); A61K 38/00 (2013.01); A61K 39/00 (2013.01); A61K 2039/57 (2013.01); A61K 2039/572 (2013.01); C12N 2770/24222 (2013.01)

(58) Field of Classification Search
CPC .................. A61K 39/0011; C07K 7/06
See application file for complete search history.

(56) References Cited

U.S. PATENT DOCUMENTS

| 9,102,715 B2* | 8/2015 | Itoh ............... A61K 39/005 |
|---|---|---|
| 2002/0128201 A1 | 9/2002 | Itoh |
| 2003/0175288 A1 | 9/2003 | Itoh |
| 2005/0130899 A1 | 6/2005 | Itoh |
| 2005/0287160 A1 | 12/2005 | Itoh et al. |
| 2006/0035291 A1 | 2/2006 | Itoh et al. |
| 2006/0140968 A1 | 6/2006 | Itoh et al. |
| 2008/0014186 A1 | 1/2008 | Itoh et al. |
| 2008/0119399 A1 | 5/2008 | Itoh et al. |
| 2008/0254445 A1 | 10/2008 | Itoh |
| 2008/0286313 A1 | 11/2008 | Itoh |
| 2010/0278851 A1 | 11/2010 | Itoh et al. |

FOREIGN PATENT DOCUMENTS

| EP | 1 090 924 | 4/2001 |
|---|---|---|
| EP | 1 116 791 | 7/2001 |
| EP | 1 908 826 | 4/2008 |
| EP | 1 982 728 | 10/2008 |
| JP | 11-318455 | 11/1999 |
| JP | 2003-000270 | 1/2003 |
| JP | 2004-000216 | 1/2004 |
| JP | 2005-99001 | 4/2005 |
| JP | 2005-162679 | 6/2005 |
| JP | 2005/170799 | 6/2005 |
| JP | 2007-145715 | 6/2007 |
| WO | 99/67288 | 12/1999 |
| WO | 00/12701 | 3/2000 |
| WO | 01/11044 | 2/2001 |
| WO | 02/10369 | 2/2002 |
| WO | 03/025569 | 3/2003 |
| WO | 03/050140 | 6/2003 |
| WO | 2004/035085 | 4/2004 |
| WO | 2005/029083 | 3/2005 |
| WO | 2005/041982 | 5/2005 |
| WO | 2005/071075 | 8/2005 |
| WO | 2005/075646 | 8/2005 |
| WO | 2005/083074 | 9/2005 |
| WO | 2005/123122 | 12/2005 |
| WO | 2007/000935 | 1/2007 |
| WO | 2007/049394 | 5/2007 |
| WO | 2007/083763 | 7/2007 |
| WO | 2007/083807 | 7/2007 |
| WO | 2008/007711 | 1/2008 |

(Continued)

OTHER PUBLICATIONS

Gomi et al., J Immunol 1999; 163:4994-5004.*
Matsumoto et al., BJU Int'l; 2010; 108:831-38.*
Yanagimoto et al., Oncol Rep. Sep. 2010;24(3):795-801.*
Hattori et al., Cancer Immunol Immunother 2009; 58:1843-52.*
Sakamoto et al., Cancer Sci. 2015; 106:1257-63.*
Noguchi et al., The Prostate 2011; DOI 10.1002/pros.21485, 12 pages.*
Takahashi et al., Cancer Sci. 2013; doi: 10.1111/cas.12226, 10 pages.*
International Search Report issued Dec. 9, 2008 in International (PCT) Application No. PCT/JP2008/066589.
Extended European Search Report issued Oct. 27, 2010 in European Application No. 08 83 2117, which is a foreign counterpart of this present application.
Yajima et al., "Immunologic Evaluation of Personalized Peptide Vaccination for Patients with Advanced Malignant Glioma", Cancer Therapy: Clinical, Clin. Cancer Res., Aug. 15, 2005, vol. 11, No. 16, pp. 5900-5911.
Mochizuki et al., "Immunological evaluation of vaccination with pre-designated peptides frequently selected as vaccine candidates in an individualized peptide vaccination regimen", International Journal of Oncology, 2004, vol. 25, No. 1, pp. 121-131.
Tsuda et al., "Vaccination with Predesignated or Evidence-Based Peptides for Patients with Recurrent Gynecologic Cancers", Clinical Studies, J. Immunother., Jan./Feb. 2004, vol. 27, No. 1, pp. 60-72.

(Continued)

Primary Examiner — Jessica H Roark
(74) Attorney, Agent, or Firm — Wenderoth, Lind & Ponack, L.L.P.

(57) ABSTRACT

The present invention provides a CTL inducer composition which comprises one or more peptides selected from the group consisting of the peptides of SEQ ID NOS: 1 to 27 in the Sequence Listing, and can be used for the treatment or prevention of cancer or a hepatitis C virus-related disease in two or more patient groups selected from the group consisting of an HLA-A2 positive patient group, an HLA-A24 positive patient group, an HLA-A26 positive patient group, and an HLA-A3 supertype positive patient group.

10 Claims, 3 Drawing Sheets

(56) References Cited

FOREIGN PATENT DOCUMENTS

| WO | 2009/022652 | 2/2009 |
|---|---|---|
| WO | 2009/038026 | 3/2009 |
| WO | 2010/050181 | 5/2010 |

OTHER PUBLICATIONS

Inoue et al., "Induction of Tumor Specific Cytotoxic T Lymphocytes in Prostate Cancer Using Prostatic Acid Phosphatase Derived HLA-A2402 Binding Peptide", The Journal of Urology, Oct. 2001, vol. 166, No. 4, pp. 1508-1513.
Yanagimoto et al., "Immunological evaluation of personalized peptide vaccination with gemcitabine for pancreatic cancer", Cancer Sci., Apr. 2007, vol. 98, No. 4, pp. 605-611.
Chang et al., "Immunopathology of hepatitis C", Springer Semin. Immunopathol., 1997, vol. 19, pp. 57-68.
Kurokohchi et al., "Use of Recombinant Protein to Identify a Motif-Negative Human Cytotoxic T-Cell Epitope Presented by HLA-A2 in the Hepatitis C Virus NS3 Region", Journal of Virology, Jan. 1996, vol. 70, No. 1, pp. 232-240.
Takao et al., "Antibody Reactive to a Hepatitis C Virus (HCV)-Derived Peptide Capable of Inducing HLA-A2 Restricted Cytotoxic T Lymphocytes is Detectable in a Majority of HCV-Infected Individuals without HLA-A2 Restriction", Microbiol. Immunol., 2004, vol. 48, No. 7, pp. 507-517.
Yamada et al., "Multidrug Resistance-associated Protein 3 is a Tumor Rejection Antigen Recognized by HLA-A2402-restricted Cytotoxic T Lymphocytes", Cancer Research, Sep. 1, 2001, vol. 61, No. 17, pp. 6459-6466.
Kobayashi et al., "Identification of a prostate-specific membrane antigen-derived peptide capable of eliciting both cellular and humoral immune responses in HLA-A24+ prostate cancer patients", Cancer Sci., Jul. 2003, vol. 94, No. 7, pp. 622-627.
Nakao et al., "Identification of a Gene Coding for a New Squamous Cell Carcinoma Antigen Recognized by the CTL", Journal of Immunology, 2000, vol. 164, No. 5, pp. 2565-2574.
Harashima et al., "Recognition of the Lck tyrosine kinase as a tumor antigen by cytotoxic T lymphocytes of cancer patients with distant metastases", Eur. J. Immunol., Feb. 2001, vol. 31, No. 2, pp. 323-332.
Minami et al., "Identification of SART3-derived peptides having the potential to induce cancer-reactive cytotoxic T lymphocytes from prostate cancer patients with HLA-A3 supertype alleles", Cancer Immunol. Immunother., May 2007, vol. 56, No. 5, pp. 689-698.
Matsueda et al., "Identification of Peptide Vaccine Candidates for Prostate Cancer Patients with HLA-A3 Supertyppe Alleles", Cancer Therapy: Preclinical, Clin. Cancer Res., Oct. 1, 2005, vol. 11, No. 19, pp. 6933-6943.
Sasada et al., "*Immediate Early Response Gene X-1*, a Stress-Inducible Antiapoptotic Gene, Encodes Cytotoxic T-Lymphocyte (CTL) Epitopes Capable of Inducing Human Leukocyte Antigen-A33-Restricted and Tumor-Reactive CTLs in Gastric Cancer Patients", Cancer Research, Apr. 15, 2004, vol. 64, pp. 2882-2888.
Takedatsu et al., "Identification of Peptide Vaccine Candidates Sharing Among HLA-A31ʹ, -A11+, -A31+ and -A33+ Cancer Patients", Clinical Cancer Research, Feb. 1, 2004, vol. 10, No. 3, pp. 1112-1120.
Naito et al., "Identification of Lck-derived peptides applicable to anti-cancer vaccine for patients with human leukocyte antigen-A3 supertype alleles", British Journal of Cancer, Dec. 17, 2007, vol. 97, No. 12, pp. 1648-1654.
Rosenberg et al., "Cancer immunotherapy: moving beyond current vaccines", Nature Medicine, Sep. 2004, vol. 10, No. 9, pp. 909-915.
Kärre et al., "Selective rejection of H-2-deficient lymphoma variants suggests alternative immune defence strategy", Nature, Feb. 1986, vol. 319, No. 20, pp. 675-678.
Storkus et al., "Reversal of natural killing susceptibility in target cells expressing transfected class I HLA genes", Proc. Natl. Acad. Sci. USA, Apr. 1989, vol. 86, pp. 2361-2364.
Hida et al., "A simple culture protocol to detect peptide-specific cytotoxic T lymphocyte precursors in the circulation", Cancer Immunol. Immunother., 2002, vol. 51, pp. 219-228.
Shorokushu, Sokai, Dai 11 Kai Society for Fundamental Cancer Immunology, May 25, 2007, p. 69.
Takashi Mine, "Personalized peptide vaccine against cancer", Surgery Frontier, 2006, vol. 13, No. 3, pp. 23-28.
The Japanese Journal of Urology, Feb. 20, 2007, vol. 98, No. 2, p. 475.
International Preliminary Report on Patentability together with Written Opinion (in English) mailed Apr. 15, 2010, in International (PCT) Application No. PCT/JP2008/066589.
Komatsu, N. Shorokushu, Sokai, Dai 11 Kai Society for Fundamental Cancer Immunology, May 25, 2007, p. 69 (in English).
Mine, T., "Personalized peptide vaccine against cancer", Surgery Frontier, 2006, vol. 13, No. 3, pp. 249-254 (in English).
Nobuaki Suzuki et al., "Detection of Peptide-Specific Cytotoxic T-Lymphocyte Precursors Used for Specific Immunotherapy of Pancreatic Cancer", Int. J. Cancer, 2002, vol. 98, pp. 45-50.
Extended European Search Report dated Oct. 13, 2014 issued in counterpart European Patent Application No. 14169857.1.
International Search Report issued Aug. 2, 2011 in International (PCT) Application No. PCT/JP2011/065033.
English translation of the International Preliminary Report on Patentability and Written Opinion in International (PCT) Application No. PCT/JP2011/065033 dated Feb. 12, 2013.
Extended European Search Report issued May 12, 2014 in corresponding European Application No. 11 80 3495.8.
Database WPI Week 200563, XP-002723175, Thomas Scientific, London, GB 2005.
Hirotsugu Uemura, et al., "Immunological Evaluation of Personalized Peptide Vaccination Monotherapy in Patients with Castration-Resistant Prostrate Cancer", Cancer Science, Mar. 2010, vol. 101, No. 3, pp. 601-608.
Yang, Damu, et al., "Identification of a Gene Coding for a Protein Possessing Shared Tumor Epitopes Capable of Inducing HLA-A24-restricted Cytotoxic T Lymphocytes in Cancer Patients", Cancer Research, vol. 59, pp. 4056-4063, 1999.
Harada, Mamoru, et al., "Prostate-Specific Antigen-Derived Epitopes Capable of Inducing Cellular and Humoral Responses in HLA-A24+ Prostate Cancer Patients", The Prostate, vol. 57, pp. 152-159, 2003.
Ogata, Rika, et al., "Identification of Polycomb Group Protein Enhancer of Zeste Homolog 2 (EZH2)-Derived Peptides Immunogenic in HLA-A24+ Prostate Cancer Patients", The Prostate, vol. 60, pp. 273-281, 2004.
Yao, A., et al., "Identification of parathyroid hormone-related protein-derived peptides immunogenic in human histocompatibility leukocyte antigen-A24+ prostate cancer patients", British Journal of Cancer, vol. 91, pp. 287-296, 2004.
Shomura, Hiroki, et al., "Identification of epidermal growth factor receptor-derived peptides recognized by both cellular and humoral immune responses in HLA-A24+ non-small cell lung cancer patients", European Journal of Cancer, vol. 40, pp. 1776-1786, 2004.
Miyagi, Yoshiaki, et al., "Induction of Cellular Immune Responses to Tumor Cells and Peptides in Colorectal Cancer Patients by Vaccination with SART3 Peptides", Clinical Cancer Research, vol. 7, pp. 3950-3962, 2001.
Komatsu, Nobukazu, et al., "Measurement of interferon-γ by high-throughput fluorometric microvolume assay technology system", Journal of Immunological Methods, vol. 263, pp. 169-176, 2002.
Noguchi, Masanori, et al., "Induction of Cellular and Humoral Immune Responses to Tumor Cells and Peptides in HLA-A24 Positive Hormone-Refractory Prostate Cancer Patients by Peptide Vaccination", The Prostate, vol. 57, pp. 80-92, 2003.
Tanaka, Shoko, et al., "Peptide Vaccination for Patients With Melanoma and Other Types of Cancer Based on Pre-existing Peptide-Specific Cytotoxic T-Lymphocyte Precursors in the Periphery", Journal of Immunotherapy, vol. 26, No. 4, pp. 357-366, 2003.
Sato, Yuji, et al., "Immunological evaluation of peptide vaccination for patients with gastric cancer based on pre-existing cellular response to peptide", Cancer Sci., vol. 94, No. 9, pp. 802-808, 2003.

(56) References Cited

OTHER PUBLICATIONS

Noguchi, Masanori, et al., "Phase I trial of patient-oriented vaccination in HLA-A2-positive patients with metastatic hormone-refractory prostate cancer", Cancer Sci., vol. 95, No. 1, pp. 77-84, 2004.
Harada, Mamoru, et al., "In Vivo Evidence That Peptide Vaccination Can Induce HLA-DR-Restricted CD4+ T Cells Reactive to a Class I Tumor Peptide", The Journal of Immunology, vol. 172, pp. 2659-2667, 2004.
Mine, Takashi, et al., "Humoral Responses to Peptides Correlate with Overall Survival in Advanced Cancer Patients Vaccinated with Peptides Based on Pre-existing, Peptide-Specific Cellular Responses", Clinical Cancer Research, vol. 10, pp. 929-937, 2004.
Sato, Y., et al., "A phase I trial of cytotoxic T-lymphocyte precursor-oriented peptide vaccines for colorectal carcinoma patients", British Journal of Cancer, vol. 90, pp. 1334-1342, 2004.
Noguchi, Masanori, et al., "Immunological Monitoring During Combination of Patient-Oriented Peptide Vaccination and Estramustine Phosphate in Patients With Metastatic Hormone Refractory Prostate Cancer", The Prostate, vol. 60, pp. 32-45, 2004.
Takedatsu, Hiroko, et al., "Expression of Epithelial Cancer-Related Antigens in Hematologic Malignancies Applicable for Peptide-Based Immunotherapy", J. Immunother, vol. 27, No. 4, pp. 289-297, 2004.
Komatsu, N., et al., "New multiplexed flow cytometric assay to measure anti-peptide antibody: a novel tool for monitoring immune responses to peptides used for immunization", Scand. J. Clin. Lab Invest., vol. 64, pp. 535-546, 2004.
Noguchi, Masanori, et al., "Immunological Evaluation of Individualized Peptide Vaccination With a Low Dose of Estramustine for HLA-A24+ HRPC Patients", The Prostate, vol. 63, pp. 1-12, 2005.
Jaeckle, Kurt A., et al., "Phase II Evaluation of Temozolomide and 13-cis-Retinoic Acid for the Treatment of Recurrent and Progressive Malignant Glioma: A North American Brain Tumor Consortium Study", Journal of Clinical Oncology, vol. 21, No. 12, pp. 2305-2311, 2003.
Prados, Michael D., "Phase 2 study of BCNU and temozolomide for recurrent glioblastoma multiforme: North American Brain Tumor Consortium study", Neuro-Oncology, vol. 6, pp. 33-37, 2004.
Rich, Jeremy N., et al., "Phase II Trial of Gefitinib in Recurrent Glioblastoma", Journal of Clinical Oncology, vol. 22, No. 1, pp. 133-142, 2004.
DeAngelis, Lisa M., "Chemotherapy for Brain Tumors—A New Beginning", The New England Journal of Medicine, vol. 352, No. 10, pp. 1036-1038, 2005.
Yagoda, Alan, et al., "Cytotoxic Chemotherapy for Advanced Hormone-Resistant Prostate Cancer," Cancer, vol. 71, pp. 1098-1109, 1993.
Scher, Howard I., et al., "Clinical Trials in Relapsed Prostate Cancer: Defining the Target", Journal of the National Cancer Institute, vol. 88, No. 22, pp. 1623-1634, 1996.
de Voogt, Herman J., et al., "Cardiovascular Side Effects of Diethylstilbestrol, Cyproterone Acetate, Medroxyprogesterone Acetate and Estramustine Phosphate Used for the Treatment of Advanced Prostatic Cancer: Results from European Organization for Research on Treatment of Cancer Trials 30761 and 30762", The Journal of Urology, vol. 135, pp. 303-307, 1986.
Tannock, Ian F., et al., "Docetaxel plus Prednisone or Mitoxantrone plus Prednisone for Advanced Prostate Cancer", The New England Journal of Medicine, vol. 351, No. 15, pp. 1502-1512, 2004.
Petrylak, Daniel P., et al., "Docetaxel and Estramustine Compared with Mitoxantrone and Prednisone for Advanced Refractory Prostate Cancer", The New England Journal of Medicine, vol. 351, No. 15, pp. 1513-1520, 2004.
Kojima, Satoko, et al., "Alternative Antiandrogens to Treat Prostate Cancer Relapse After Initial Hormone Therapy", The Journal of Urology, vol. 171, pp. 679-683, 2004.
Salgaller, Michael L., et al., "Immunization against Epitopes in the Human Melanoma Antigen gp100 following Patient Immunization with Synthetic Peptides", Cancer Research, vol. 56, pp. 4749-4757, 1996.
Rosenberg, Steven A., et al., "Immunologic and therapeutic evaluation of a synthetic peptide vaccine for the treatment of patients with metastatic melanoma", Nat. Med., vol. 4, No. 3, pp. 321-327, 1998.
Nestle, Frank O., et al., "Vaccination of melanoma patients with peptide- or tumor lysate-pulsed dendritic cells", Nature Medicine, vol. 4, No. 3, pp. 328-332, 1998.
Marchand, Marie, et al., "Tumor Regressions Observed in Patients with Metastatic Melanoma Treated With an Antigenic Peptide Encoded by Gene MAGE-3 and Presented by HLA-A1", Int. J. Cancer, vol. 80, pp. 219-230, 1999.
Slingluff, Jr., Craig L., et al., "Phase I Trial of a Melanoma Vaccine with gp100$_{280-288}$ Peptide and Tetanus Helper Peptide in Adjuvant: Immunologic and Clinical Outcomes", Clinical Cancer Research, vol. 7, pp. 3012-3024, 2001.
Wang, Flora, et al., "Phase I Trial of a MART-1 Peptide Vaccine with Incomplete Freund's Adjuvant for Resected High-Risk Melanoma", Clinical Cancer Research, vol. 5, pp. 2756-2765, 1999.
Jäger, Elke, et al., "Induction of primary NY-ESO-1 immunity: CD8+ T lymphocyte and antibody responses in peptide-vaccinated patients with NY-ESO-1+ cancers", PNAS, vol. 97, No. 22, pp. 12198-12203, 2000.
Tsugawa, T., et al., "Sequential delivery of interferon-α gene and DCs to intracranial gliomas promotes an effective antitumor response", Gene Therapy, vol. 11, pp. 1551-1558, 2004.
"The Committee of Brain Tumor Registry of Japan: Report of Brain Tumor Registry of Japan (1969-1993)", 10$^{th}$ Edition, Neurol. Medcio-Chirurgica, vol. 40 (suppl), pp. 1-106, 2000.
Kitamura, Tadaichi, "Necessity of re-evaluation of estramustine phosphate sodium (EMP) as a treatment option for first-line monotherapy in advanced prostate cancer", International Journal of Urology, vol. 8, pp. 33-36, 2001.
Noguchi, Masanori, et al., "Combination Therapy for Personalized Peptide Vaccination and Low-Dose Estramustine Phosphate for Metastatic Hormone Refractory Prostate Cancer Patients: An Analysis of Prognostic Factors in the Treatment", Oncology Research, vol. 16, pp. 341-349, 2007.
Murayama, Kumiko, et al., "Expression of the SART3 Tumor-Rejection Antigen in Brain Tumors and Induction of Cytotoxic T Lymphocytes by Its Peptides", Journal of Immunotherapy, vol. 23, No. 5, pp. 511-518, 2000.
Homma, Shigenori, et al., "Differential levels of human leukocyte antigen-class I, multidrug-resistance 1 and androgen receptor expressions in untreated prostate cancer cells: The robustness of prostate cancer", Oncology Reports, vol. 18, pp. 343-346, 2007.
Noguchi, Masanori, et al., "A randomized phase II trial of personalized peptide vaccine plus low dose estramustine phosphate (EMP) versus standard dose EMP in patients with castration resistant prostate cancer", Cancer Immunol. Immunother, vol. 59, No. 7, pp. 1001-1009, 2010.
Noguchi, Masanori, et al., "Immunological Evaluation of Neoadjuvant Peptide Vaccination Before Radical Prostatectomy for Patients With Localized Prostate Cancer", The Prostate, vol. 67, pp. 933-942, 2007.
Naito, Masayasu, et al., "Dexamethasone Did Not Suppress Immune Boosting by Personalized Peptide Vaccination for Advanced Prostate Cancer Patients", The Prostate, vol. 68, pp. 1753-1762, 2008.
Roger Stupp, M.D., et al.; "Radiotherapy plus Concomitant and Adjuvant Temozolomide for Glioblastoma", The New England Journal of Medicine, vol. 352, No. 10, pp. 987-996, 2005.
Itoh et al., Jpn. J. Clin. Oncol. 2009; 39(2):73-80.
Nagorsen & Thiel, Cancer Immunol. Immunother 2008; 57:1903-10.
Terasaki et al., Cancer Immunol Immunother 2009; 58:1877-85.
Frahm et al., Eur. J. Immunol. 2007; 37: 2419-33.
Burrows et al., J. Immunol 2003;171:1407-12.
Kataja et al., Ann Oncol 2009; 20(sup 4): iv10-14.
Nelson et al., Ann. Intern. Med. 2009;151:727-737.
Balmana et al., Ann. Oncol. 2009; 20(sup 4): iv19-20.

* cited by examiner

CTL INDUCER COMPOSITION

TECHNICAL FIELD

The present invention relates to a CTL inducer composition comprising a peptide useful for the treatment or prevention of cancer or a hepatitis C virus-related disease in a plurality of patient groups having different HLA types.

BACKGROUND ART

Malignant tumors are the leading cause of Japanese deaths, accounting for about 310,000 deaths a year. In the world, cancer causes death of about six million people a year. Cancer treatments employ surgical resection, anti-cancer agents, radiotherapy, and others. However, these treatment regimens involve problems, such as recurrence, problems in QOL, and in addition, the lack of treatment options in cases of advanced cancer to which these treatments are not administered. As a fourth treatment regimen, immunotherapy for cancer (vaccine therapy) has been eagerly expected for a long time. Clinical studies of peptide vaccines were begun in the world in 1990, when human cancer antigen peptides became identifiable. According to the summarized results of clinical studies by administrating peptides alone or in combined therapies, however, the rate of effectiveness was 2.7% in more than 1,000 cases (Nature Immunology, 2004), and it is turning out that it is difficult to formulate them into pharmaceutical preparations.

The present inventors, on the other hand, have conducted tailor-made peptide vaccine therapy, in which the HLA type and specific immune responses of patients were examined in advance to select a peptide vaccine to be administered, and ascertained that the peptide vaccines are safe and effective. Specifically, clinical effects were observed against brain tumors and cervical cancer by administration of tailor-made peptide vaccines alone (Non-Patent Documents 1 to 3). Moreover, their use in combination with anti-cancer agents resulted in excellent clinical effects and safety being achieved in prostate and pancreas cancers, at levels allowing for formulating them into pharmaceutical preparations (Non-Patent Documents 4 and 5).

The cellular immunity by specific T-cells which are thought to be the principal effector in cancer peptide vaccine therapy is human leukocyte antigen (HLA)-restricted, and based on this, researchers in the world, including the present inventors, have carried out the development of vaccines to be given only to patients having specific HLA types (HLA-A2 and HLA-A24). However, the percentage of patients having these two HLA types is on the order of 40 to 75%, and thus the remaining, 25 to 60% patients having less frequent HLA types cannot be benefit from the effects of peptide vaccines. Therefore, there is a need for research on the development of peptide vaccines which can be applied to cancer patients in the world.

There have already been identified peptides which bind to any of HLA-A24, -A2, -A26, and HLA-A3 supertypes (HLA-A3, -A11, -A31, -A33, and -A68.1) and are capable of inducing HLA-restricted CTLs for the respective HLAs. These peptides have been reported to be useful as peptide vaccines against cancer (Patent Documents 1 to 13 and Non-Patent Documents 1 to 17).

In clinical tests, which are being conducted by the present inventor, of cancer vaccines using tailor-made peptides, based on these findings, the HLA type of a patient is examined beforehand, and according to the HLA type of the patient, a maximum four peptides are selected from candidate peptides and administered. Thus, when the HLA type of a patient is HLA-A2-A24, peptides are selected from sets of 8 peptides for HLA-A2 and HLA-A24, respectively, that is 16 peptides. In the case where a patient is homozygous for HLA-A24, however, peptides should be selected among 8 peptides for A24. It is very difficult to introduce additional types of peptides which can be cancer vaccines. Therefore, by determining whether peptides can induce HLA-restricted CTLs across different groups, the choice of peptides can be expanded for patients having specific HLA types.

Meanwhile, pathological mechanism of hepatocellular disorders after hepatitis C virus (HCV) infection is not yet understood well, but many lines of evidence show that virus-specific cytotoxic T lymphocytes (CTLs) may play a key role on disorders of the liver after HCV infection (Non-Patent Document 6). It is also suggested that CTLs are effective for limiting spreading of the virus and eliminating the virus during viral infection (Non-Patent Document 7). Therefore, the induction of CTLs with vaccines would be a promising strategy for controlling diseases associated with HCV infection. Thus, there is a need for developing peptide vaccines which are intended to induce CTLs, because of their reduced cost and storage with ease.

The present inventors previously observed that the C35-44 peptide, a peptide derived from the sequence of the HCV core protein, of which the sequence is YLLPRRGPRL (SEQ ID NO: 25), can induce CTLs in patients positive for HLA-A24 or -A3 supertype (Patent Document 14). Prior to this observation, this C35-44 peptide had also been reported to be capable of strong induction of CTLs useful for eliminating the virus from the peripheral blood of HLA-A2 positive individuals (Non-Patent Document 8 and Patent Document 15).

The documents cited in the present invention are as listed below. The documents described below are incorporated in this patent application by reference.

Patent Document 1: International Publication No. WO 2005/071075
Patent Document 2: International Publication No. WO 01/011044
Patent Document 3: Japanese Unexamined Patent Publication (Kokai) No. 2003-270
Patent Document 4: International Publication No. WO 2003/050140
Patent Document 5: Japanese Unexamined Patent Publication (Kokai) No. Hei 11-318455 (1999)
Patent Document 6: International Publication No. WO 00/12701
Patent Document 7: International Publication No. WO 02/010369
Patent Document 8: International Publication No. WO 99/67288
Patent Document 9: Japanese Patent Application No. 2007-2127179
Patent Document 10: Japanese Unexamined Patent Publication (Kokai) No. 2004-216
Patent Document 11: International Publication No. WO 2007/000935
Patent Document 12: International Publication No. WO 2005/075646
Patent Document 13: International Publication No. WO 2008/007711
Patent Document 14: International Publication No. WO 2007/083807
Patent Document 15: International Publication No. WO 2007/049394

Non-Patent Document 1: Yajima N et al., Clin Cancer Res. 2005 Aug. 15; 11(16):5900-11

Non-Patent Document 2: Mochizuki K et al., Int J Oncol. 2004 July; 25(1):121-31

Non-Patent Document 3: Tsuda N et al., J Immunother. 2004 January-February; 27(1):60-72

Non-Patent Document 4: Inoue Y et al., J Urol. 2001 October; 166(4):1508-13. Erratum in: J Urol. 2002 May; 167(5):2146

Non-Patent Document 5: Yanagimoto H et al., Cancer Sci. 2007 April; 98(4): 605-11. Epub 2007 Feb. 19

Non-Patent Document 6: Chang K M et al, Springer Semin Immunopathol. 1997; 19:57-68

Non-Patent Document 7: Kurokohchi K et al., J. Virol. 1996; 70:232-240

Non-Patent Document 8: Takao Y. et al., Microbiol. Immunol., 48(7), 507-517, 2004

Non-Patent Document 9: Yamada A et al., Cancer Res. 2001 Sep. 1; 61(17):6459-66

Non-Patent Document 10: Kobayashi K et al., Cancer Sci. 2003 July; 94 (7):622-7

Non-Patent Document 11: Nakao M et al., J Immunol. 2000 Mar. 1; 164 (5):2565-74

Non-Patent Document 12: Harashima N et al., Eur J Immunol. 2001 February; 31(2):323-32

Non-Patent Document 13: Minami T et al., Cancer Immunol. Immunother. 2007, May 56(5) 689-98

Non-Patent Document 14: Matsueda S et al., Clin Cancer Res. 2005 Oct. 1; 11(19 Pt 1):6933-43

Non-Patent Document 15: Takedatsu H et al., Clin Cancer Res. 2004 Feb. 1; 10(3):1112-20

Non-Patent Document 16: Naito M et al., Br J Cancer. 2007 Dec. 17; 97(12):1648-54. Epub 2007 Nov. 27

DISCLOSURE OF THE INVENTION

Problems to be Solved by the Invention

An object of the present invention is to provide a peptide capable of inducing HLA-restricted CTLs so for a plurality of HLA types.

Means for Solving the Problems

An object of the present invention is to provide a CTL inducer composition comprising a peptide, wherein the peptide is a known peptide which has been reported to have the ability to induce HLA-restricted CTLs for HLA-A24, HLA-A2, or HLA-A3 supertype and wherein the peptide can induce HLA-restricted CTLs for two or more HLA types including an HLA type(s) other than that already reported.

Therefore, the present invention provides a CTL inducer composition which comprises one or more peptides and can be used for the treatment or prevention of cancer and/or a disease caused by hepatitis C virus in two or more patient groups, wherein the one or more peptides are selected from the group consisting of EGFR-800 (SEQ ID NO: 1), Lck-208 (SEQ ID NO: 2), Lck-488 (SEQ ID NO: 3), MRP3-1293 (SEQ ID NO: 4), PAP-213 (SEQ ID NO: 5), PSA-248 (SEQ ID NO: 6), SART2-93 (SEQ ID NO: 7), SART3-109 (SEQ ID NO: 8), SART3-302 (SEQ ID NO: 9), Lck-246 (SEQ ID NO: 10), ppMAPkkk-432 (SEQ ID NO: 11), WHSC2-103 (SEQ ID NO: 12), UBE-43 (SEQ ID NO: 13), HNRPL-501 (SEQ ID NO: 14), CypB-129 (SEQ ID NO: 15), Lck-422 (SEQ ID NO: 16), Lck-449 (SEQ ID NO: 17), β-tubulin5-154 (SEQ ID NO: 18), Lck-90 (SEQ ID NO: 19), PSA-16 (SEQ ID NO: 20), PAP-248 (SEQ ID NO: 21), IEX1-47 (SEQ ID NO: 22), SART3-511 (SEQ ID NO: 23), SART3-734 (SEQ ID NO: 24), C35-44 (SEQ ID NO: 25), PAP-155 (SEQ ID NO: 26), and β-tubuline-309 (SEQ ID NO: 27), and wherein the two or more patient groups are selected from the group consisting of an HLA-A2 positive patient group, an HLA-A24 positive patient group, an HLA-A26 positive patient group, and an HLA-A3 supertype positive patient group.

The present invention also provides a pharmaceutical composition which is a composition comprising one or more peptides and can be used for the treatment or prevention of cancer in two or more patient groups, wherein the one or more peptides are selected from the group consisting of EGFR-800 (SEQ ID NO: 1), Lck-208 (SEQ ID NO: 2), Lck-488 (SEQ ID NO: 3), MRP3-1293 (SEQ ID NO: 4), PAP-213 (SEQ ID NO: 5), PSA-248 (SEQ ID NO: 6), SART2-93 (SEQ ID NO: 7), SART3-109 (SEQ ID NO: 8), SART3-302 (SEQ ID NO: 9), Lck-246 (SEQ ID NO: 10), ppMAPkkk-432 (SEQ ID NO: 11), WHSC2-103 (SEQ ID NO: 12), UBE-43 (SEQ ID NO: 13), HNRPL-501 (SEQ ID NO: 14), CypB-129 (SEQ ID NO: 15), Lck-422 (SEQ ID NO: 16), Lck-449 (SEQ ID NO: 17), β-tubulin5-154 (SEQ ID NO: 18), Lck-90 (SEQ ID NO: 19), PSA-16 (SEQ ID NO: 20), PAP-248 (SEQ ID NO: 21), IEX1-47 (SEQ ID NO: 22), SART3-511 (SEQ ID NO: 23), SART3-734 (SEQ ID NO: 24), PAP-155 (SEQ ID NO: 26), and β-tubulin-309 (SEQ ID NO: 27), and wherein the two or more patient-populations are selected from the group consisting of an HLA-A2 positive patient group, an HLA-A24 positive patient group, an HLA-A26 positive patient group, and an HLA-A3 supertype positive patient group.

The composition of the present invention comprising one or more peptides selected from the group consisting of EGFR-800 (SEQ ID NO: 1), Lck-488 (SEQ ID NO: 3), SART2-93 (SEQ ID NO: 7), SART3-109 (SEQ ID NO: 8), WHSC2-103 (SEQ ID NO: 12), UBE-43 (SEQ ID NO: 13), HNRPL-501 (SEQ ID NO: 14), CypB-129 (SEQ ID NO: 15), and PAP-155 (SEQ ID NO: 26) can induce HLA-restricted CTLs for both HLA-A24 and HLA-A2, and can be used for the treatment or prevention of an HLA-A24 positive cancer patient group and an HLA-A2 positive cancer patient group.

The composition of the present invention comprising one or more peptides selected from the group consisting of EGFR-800 (SEQ ID NO: 1), SART2-93 (SEQ ID NO: 7), SART3-109 (SEQ ID NO: 8), WHSC2-103 (SEQ ID NO: 12), UBE-43 (SEQ ID NO: 13), HNRPL-501 (SEQ ID NO: 14), β-tubulin5-154 (SEQ ID NO: 18), Lck-90 (SEQ ID NO: 19), and IEX1-47 (SEQ ID NO: 22), PAP-155 (SEQ ID NO: 26) and β-tubuline-309 (SEQ ID NO: 27) can induce HLA-restricted CTLs for both HLA-A24 and HLA-A3 supertype, and can be used for the treatment or prevention of an HLA-A24 positive cancer patient group and an HLA-A3 supertype positive cancer patient group.

The composition of the present invention comprising one or more peptides selected from the group consisting of SART2-93 (SEQ ID NO: 7), SART3-109 (SEQ ID NO: 8), Lck-246 (SEQ ID NO: 10), ppMAPkkk-432 (SEQ ID NO: 11), WHSC2-103 (SEQ ID NO: 12), UBE-43 (SEQ ID NO: 13), HNRPL-501 (SEQ ID NO: 14), Lck-422 (SEQ ID NO: 16), Lck-90 (SEQ ID NO: 19), and SART3-511 (SEQ ID NO: 23) can induce HLA-restricted CTLs for both HLA-A2 and HLA-A3 supertype, and can be used for the treatment or prevention of an HLA-A2 positive cancer patient group and an HLA-A3 supertype positive cancer patient group.

The composition of the present invention comprising one or more peptides selected from the group consisting of SART2-93 (SEQ ID NO: 7), SART3-109 (SEQ ID NO: 8), WHSC2-103 (SEQ ID NO: 12), UBE-43 (SEQ ID NO: 13), and HNRPL-501 (SEQ ID NO: 14) can induce HLA-restricted CTLs for HLA-A2, HLA-A24, and HLA-A3 supertype, and can be used for the treatment or prevention of an HLA-A2 positive cancer patient group, an HLA-A24 positive cancer patient group, and an HLA-A3 supertype positive cancer patient group.

The composition of the present invention comprising one or more peptides selected from the group consisting of EGFR-800 (SEQ ID NO: 1), ppMAPkkk-432 (SEQ ID NO: 11), HNRPL-501 (SEQ ID NO: 14), and SART3-109 (SEQ ID NO: 8) can induce HLA-restricted CTLs for HLA-A26, and can also be used for the treatment or prevention of an HLA-A26 positive cancer patient group, in addition to the above-described patient groups.

The composition of the present invention comprising the peptide C35-44 (SEQ ID NO: 25) can be used for the treatment or prevention of a hepatitis C virus-related disease in HLA-A24 positive patients, HLA-A2 positive patients, HLA-A3 supertype positive patients, and HLA-A26 positive patients, that is, the treatment or prevention of patient groups of hepatitis, cirrhosis, and liver cancer associated with HCV infection.

Effects of the Invention

The peptide contained in the CTL inducer compositions of the present invention has the ability to induce HLA-restricted CTLs for a plurality of HLA types, and thus can be used for the treatment or prevention of cancer and a hepatitis C infection-related disease in patients having an HLA type other than the HLA types for which the peptide is previously known to induce HLA-restricted CTLs. The present invention provides a wider range of selection of peptides for patients with the respective HLA types, and allows carrying out more efficient treatments in tailor-made cancer vaccine therapy.

In addition, a CTL inducer composition comprising the peptide represented by C35-44 (SEQ ID NO: 25) is capable of inducing CTLs in any of an HLA-A24 positive patient, an HLA-A2 positive patient, an HLA-A3 supertype positive patient, and an HLA-A26 positive patient and can be used for the treatment or prevention of hepatitis C virus-related diseases.

BEST MODE FOR CARRYING OUT THE INVENTION

Figure 1:
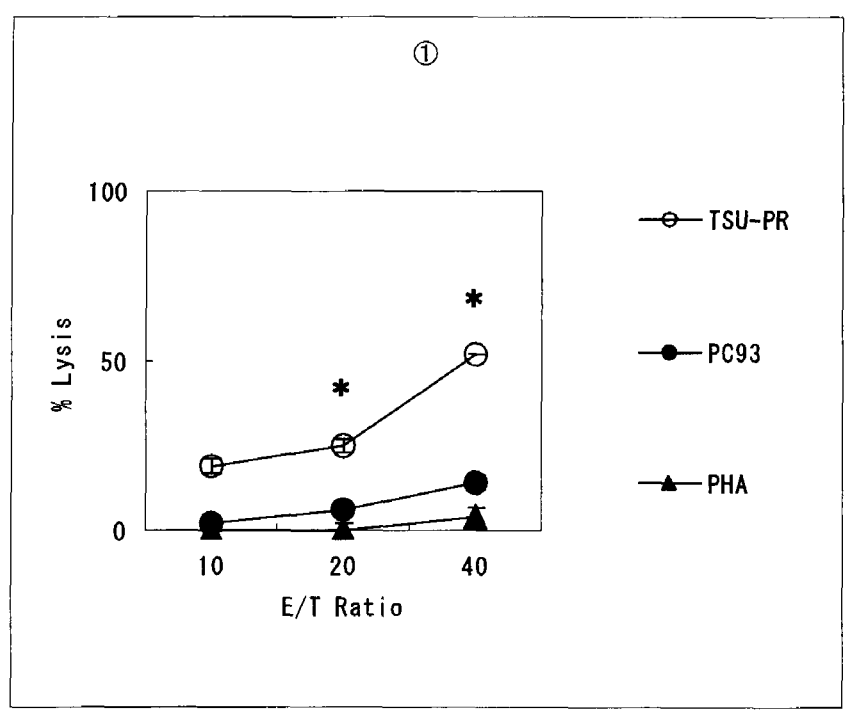
FIG. 1 shows cytotoxic activities of CTLs obtained by stimulating PBMCs from HLA-A11 positive cancer patients with HLA-A24-binding SART3-109.

By "binding to two or more HLA molecules selected from the group consisting of HLA-A24, HLA-A2, HLA-A3 supertype, and HLA-A26" is meant that a peptide can form a complex with two or more HLA molecules selected from the group consisting of molecules included in HLA-A24, HLA-A2, HLA-A3 supertype, and HLA-A26 molecules and can be represented on the cell surface.

In the present invention, the ability to induce peptide-specific CTLs can be examined, for example, by stimulating peripheral blood mononuclear cells (PBMCs) with a peptide and determining, by means of ELISA methods or the like, whether the peptide-stimulated PBMCs respond to antigen presenting cells pulsed with the corresponding peptide and produce cytokines (for example, IFN-γ). In addition, the cytotoxic activity of induced CTLs can be ascertained by $^{51}$Cr release assay methods and others.

The peptides of the present invention can be produced by conventional peptide synthesis. Methods for such purposes include methods described, for example, in Peptide Synthesis, Interscience, New York, 1966; The Proteins, Vol. 2, Academic Press Inc., New York, 1976; Peptide Synthesis [in Japanese], MARUZEN Co., Ltd., 1975; Basics And Experiments In Peptide Synthesis [in Japanese], MARUZEN Co., Ltd., 1985; and Development Of Pharmaceuticals, Second Series, Vol. 14, Peptide Synthesis [in Japanese], Hirokawa Shoten Co., 1991.

The peptide contained in the CTL inducer composition of the present invention may be generated by intracellular fragmentation of a polypeptide comprising the amino acid sequence of the peptide of the present invention. The present invention also encompasses the use of the peptide of the present invention in such an embodiment. The number of amino acid residues and the amino acid sequence of such a polypeptide can be selected as desired, without any limitation, as long as the polypeptide can provide the peptide of the present invention.

The peptide contained in the CTL inducer composition of the present invention can efficiently induce and proliferate CTLs which specifically kill cancer cells in two or more patient groups selected from the group consisting of HLA-A24, HLA-A2, HLA-A3 supertype, and HLA-A26 positive patient groups, and thus is useful for treating a wide variety of cancer patients.

The present invention provides a pharmaceutical composition for the treatment or prevention of cancer, comprising the peptide as specified above. The pharmaceutical composition for the treatment or prevention of cancer according to the present invention may comprise a single peptide, or two or more peptides and/or derivatives thereof in combination. Since CTLs from a cancer patient are a subset of cells which recognize different cancer-antigen peptides, it is further effective to use a plurality of cancer-antigen peptides and/or derivatives thereof in combination. The peptide of the present invention may also be combined with a cancer antigen peptide other than that of the present invention.

The pharmaceutical composition for the treatment or prevention of cancer according to the present invention may comprise pharmaceutical preparations which contain plural peptides, for example, eight peptides including the peptide(s) of the present invention, separately, in order that the composition could be used in tailor-made therapy.

The pharmaceutical composition of the present invention can comprise, in addition to the peptide(s), pharmaceutically acceptable carriers and the like. Used as carriers can be celluloses, polymerized amino acids, albumin, and others. The pharmaceutical composition of the present invention may include liposome formulations, particulate formulations bound to beads having diameters of several micrometers, formulations bound to lipids, and the like. The pharmaceutical composition of the present invention can also be administered in conjunction with adjuvants known previously to be used for vaccination, such that immune responses are effectively established. Methods for administration include, for example, intradermal or subcutaneous administration, and or the like.

The pharmaceutical composition for the treatment or prevention of cancer according to the present invention can be used as a cancer vaccine. Dosage amounts can be adjusted as appropriate, depending on the condition of a disease, the age and weight of the individual patients, and the like. Usually, the amount of the peptide in the pharmaceutical composition usually ranges from 0.0001 to 1000 mg, preferably from 0.001 to 100 mg, more preferably from 0.01 to 10 mg, even more preferably from 0.1 to 5 mg or 0.5 to 3 mg, which is preferably administered repeatedly, once per several days, weeks, or months.

The present invention also provides a method of inducing cancer-reactive CTLs, comprising contacting peripheral blood mononuclear cells (PBMCs) collected from a cancer patient group positive for HLA-A24, HLA-A2, HLA-A26, or HLA-A3 supertype with the peptide of the present invention. The peptide of the present invention can induce CTLs from PBMCs derived from two or more of the above-described cancer patient groups. "Cancer-reactive" with respect to CTLs means that CTLs recognize a complex of a cancer antigen peptide on a target cancer cell and an HLA molecule and is capable of killing the cancer cell. Induction of CTLs is carried out, for example, by in vitro culturing PBMCs collected from a malignant brain-tumor patient positive for HLA-A24, in the presence of a peptide of the present invention. The method for inducing CTLs according to the present invention is useful for adoptive immunotherapy wherein the induced CTLs are returned back into the patient from whom the PBMCs were collected to kill cancer cells.

The present invention also provides a kit for inducing CTLs, which is used for carrying out the said method for inducing CTLs. The kit of the present invention comprises one or more of the peptides of the present invention, and may further comprise an appropriate buffer, medium, and the like.

The present invention also provides a method for preparing antigen presenting cells, wherein the antigen presenting cells can induce CTLs which are cytotoxic against a cancer cell selected from the group consisting of an HLA-A24 positive cancer cell, an HLA-A2 positive cancer cell, an HLA-A26 positive cancer cell, and an HLA-A3 supertype positive cancer cell. The method for preparing antigen presenting cells according to the present invention is carried out, for example, by culturing cells having the ability of antigen presentation derived from an HLA-A24 positive cancer patient with the peptide of the present invention, such that the peptide is allowed bind to the HLA-A24 molecule and to be presented. In an alternative, a vector capable of expressing such a peptide may be introduced into cells having the ability of antigen presentation derived from an HLA-A24 positive cancer patient to express the peptide. Cells having the ability of antigen presentation include, for example, dendritic cells. Dendritic cells derived from a patient can be obtained, for example, by separating culture-plate-adherent cells from PBMCs collected from a patient and culturing the adherent cells for about one week in the presence of IL-4 and GM-CSF. The antigen presenting cells prepared by the method of the present invention can induce CTLs which specifically recognize a complex of a peptide and an HLA molecule which is presented on a cell surface in two or more cells selected from the group consisting of an HLA-A24 positive cancer cell, an HLA-A2 positive cancer cell, and an HLA-A3 supertype positive cancer cell, and when administered to a cancer patient, can facilitate the induction of cancer-reactive CTLs within the cancer patient. That is, the antigen presenting cells prepared by the method of the present invention can be used as pharmaceutical use for the treatment or prevention of cancer.

The present invention also provides a kit for preparing antigen presenting cells, which is used for carrying out the said method for preparing antigen presenting cells. The kit of the present invention comprises one or more of the peptides and/or derivatives thereof of the present invention and may further comprise an appropriate buffer, medium, and the like.

The present invention also provide a CTL inducer composition which comprises a peptide C35-44 (SEQ ID NO: 25), and is useful for the treatment or prevention of a hepatitis C virus-related disease in an HLA-A24 positive patient, an HLA-A2 positive patient, and an HLA-A3 supertype positive patient. In the present invention, "hepatitis C virus-related disease" is intended to include not only hepatitis C, but also all diseases caused due to HCV infection, such as cirrhosis and liver cancer.

The present invention is described in more detail with reference to the following Examples, which are not intended to limit the present invention thereto in any way.

The present inventors examined, for the ability to bind to other HLA types, a total of 34 peptides known to be capable of inducing HLA-restricted CTLs for any of HLA-A24, HLA-A2, HLA-A26, and HLA-A3 supertype (13, 9, and 12 peptides, respectively).

Table 1 indicates the peptides examined by the present inventors and their known HLA-binding properties.

TABLE 1

| Known HLA-Binding Property | Name | Peptide | SEQ ID NO: | Document |
|---|---|---|---|---|
| A24 | EGFR-800 | DYVREHKDNI | 1 | Patent Document 1 |
|  | Lck-208 | HYTNASDGL | 2 | Patent Document 2 |
|  | Lck-488 | DYLRSVLEDF | 3 | Patent Document 2 |
|  | MRP3-1293 | NYSVRYRPGL | 4 | Patent Document 3 |
|  | PAP-213 | LYCESVHNF | 5 | Non-Patent Document 4 |
|  | PSA-248 | HYRKWIKDTI | 6 | Patent Document 4 |

TABLE 1-continued

| Known HLA-Binding Property | Name | Peptide | SEQ ID NO: | Document |
|---|---|---|---|---|
| | SART2-93 | DYSARWNEI | 7 | Patent Document 5 |
| | SART3-109 | VYDYNCHVDL | 8 | Patent Document 6 |
| | MRP503 | LYAWEPSFL | 28 | Non-Patent Document 9 |
| | PSM 624 | TYSVSFDSL | 29 | Non-Patent Document 10 |
| | PAP 213 | LYCESVHNF | 30 | Non-Patent Document 11 |
| | SART2 161 | AYDFLYNYL | 31 | Non-Patent Document 4 |
| | Lck-246 | TFDYLRSVL | 32 | Non-Patent Document 12 |
| A2 | SART3-302 | LLQAEAPRL | 9 | Patent Document 6 |
| | Lck-246 | KLVERLGAA | 10 | Patent Document 2 |
| | ppMAPKKK-432 | DLLSHAFFA | 11 | Patent Document 7 |
| | WHSC2-103 | ASLDSDPWV | 12 | Patent Document 7 |
| | UBE-43 | RLQEWCSVI | 13 | Patent Document 7 |
| | HNRPL-501 | NVLHFFNAPL | 14 | Patent Document 7 |
| | CypB-129 | KLKHYGPGWV | 15 | Patent Document 8 |
| | Lck-422 | DVWSFGILL | 16 | Patent Document 2 |
| | C35-44 | YLLPRRGPRL | 25 | Patent Document 13 |
| A3 | Lck-449 | VIQNLERGYR | 17 | Patent Document 9 |
| | β-tublin5-154 | KIREEYPDR | 18 | Patent Document 10 |
| | Lck-90 | ILEQSGEWWK | 19 | Patent Document 9 |
| | PSA-16 | GAAPLILSR | 20 | Patent Document 11 |
| | PAP-248 | GIHKQKEKSR | 21 | Patent Document 11 |
| | IEX1-47 | APAGRPSASR | 22 | Patent Document 12 |
| | SART3-511 | WLEYYNLER | 23 | Non-Patent Document 13 |
| | SART3-734 | QIRPIFSNR | 24 | Non-Patent Document 13 |
| | PAP 155 | YLPFRNCPR | 26 | Non-Patent Document 14 |
| | β-tubline 309 | KIREEYPDR | 27 | Non-Patent Document 15 |
| | Lck 450 | IQNLERGYR | 33 | Non-Patent Document 16 |
| | CGI 37 | KFTKTHKFR | 34 | Non-Patent Document 15 |

Peptides

The peptides listed in Table 1 were prepared.

All these peptides were at purities of >90% and purchased from Biologica Co. (Nagoya, Japan). Gag77-85 (SLYNT-VATL) (SEQ ID NO: 35) was used as a control peptide binding to HLA-A2 type, env-GP (RYLRDQQLL) (SEQ ID NO: 36) as a control peptide binding to HLA-A24 type, HIV-Gag167-175 (EVIPMFSAL) (SEQ ID NO: 37) as a control peptide binding to HLA-A26 type, and an HIV-derived peptide (RLRDLLLIVTR) (SEQ ID NO: 38) as a control peptide binding to HLA-A3 supertype allele molecule. The peptides were all dissolved at a dose of 10 μg/ml using dimethyl sulfoxide.

Five HLA-A alleles included in the HLA-A3 supertype share a binding motif, but HLA-A3 or HLA-A68.1 positive Japanese individuals are vary rare. In this study, therefore, the peptides were examined for the ability to bind to HLA-A11, -A31, and -A33 molecules.

Patients (PTs)

Cancer patients were included who were positive for any HLA of HLA-A2, HLA-A24, HLA-A26, HLA-A11, HLA-A31, and HLA-A33.

Healthy Donors (HDs)

Healthy donors included HLA-A2 positive, HLA-A24 positive, HLA-A26 positive, HLA-A11 positive, HLA-A31 positive, and HLA-A33 positive patients.

All of the patients and healthy donors from whom PBMCs were collected were not HIV-infected. Twenty milliliters of peripheral blood was collected from a patient/healthy donor to prepare PBMCs by Ficoll-Conray gradient centrifugation.

All samples were stored at low temperatures until used in experiments. Expression of HLA-A2, HLA-A24, HLA-A11, -A31, and -A33 molecules on PBMCs was confirmed by flow cytometry using the following antibodies: anti-HLA-A24 monoclonal antibody (mAb), anti-HLA-A2 mAb, anti-HLA-A26 mAb, anti-HLA-A11 mAb, anti-HLA-A31 mAb, anti-HLA-A33 mAb (all available from One Lambda, Calif., USA); and FITC-conjugated anti-mouse immunoglobulin G (IgG) mAb.

Cell Lines

T2 cells expressing HLA-A2 were obtained from ATCC (CRL-1992). C1R-A24, C1R-A26, C1R-A11, C1R-A31, and C1R-A33 are cells generated from C1R parent cell line transfected with the HLA-A24, HLA-A26, HLA-A11, HLA-A31, and HLA-A33 genes so as to express the corresponding HLA molecules, respectively (Takedatsu et al., Clin Cancer Res 2004; 10:111220). The C1R parent cells are human B-lymphoblast (HMy2.CIR: Human B lymphoblast; ATCC CRL-1993) and are of a cell line obtained by irradiating γ-ray to HMy.2 B lymphoblastoid cell line and selecting a cell expressing MHC class I-Cw4 and lacking HLA class I-A and -B by antibodies and complements (Storkus W J, Alexander J, Payne J A, Dawson J R, and Cresswell P, Procnatl acad sci USA, 86:2361-2364, 1989).

RMA-S-A2601 is a stable transfectant cell generated by introducing the HLA-A2601 gene into RMA-S cells (a cell separated as a variant RMA cell displaying low expression of MHC class-I molecules on the cell membrane: Karre K, Ljunggren H-G, Piontek G, and Kiessling R. 1986, Selective rejection of H-2-deficient lymphoma variants suggest alternative immune defence strategy. Nature (Lond) 319: 675).

PC-93 is a prostate sarcoma cell line and is negative for HLA-A11. TSU-PR is a prostate cancer cell line and is positive for HLA-A11. SQ-1 is a lung cancer cell line and is negative for HLA-A11. COLO-201 is a colon cancer cell line and is positive for HLA-A11. LC-1 is a lung cancer cell line and is positive for HLA-A31/HLA-A33. All of these tumor cell lines were cultured in RPMI 1640 (Invitrogen) containing 10% FCS.

Induction of Peptide-Reactive CTLs from PBMCs

Peptide-reactive CTLs were detected by the method previously reported with some modifications (Hida N, Maeda Y, Katagiri K, Takasu H, Harada M, Itoh K., Cancer Immunol Immunother 2002; 51:219-28). PBMCs obtained in a routine procedure from each of patients (PTs) and healthy donors (HDs) were stimulated in vitro with the respective peptides or control peptides. The resulting peptide-stimulated PBMCs were co-cultured with T2, C1R-A24, -A26, -A11, C1R-A31, or C1R-A33 cells pulsed with the same peptide as that used for the peptide stimulation of PBMCs and measured for the amount of IFN-γ produced, which was used as an index of CTL induction.

Specifically, PBMCs (1×10$^5$ cells/well) were incubated with each of the peptides (10 μl/ml), in a set of 4 wells, in 200 μl of culture medium in U-bottom 96-well micro-culture plates (Nunc, Roskilde, Denmark). The culture medium was composed of 45% RPMI 1640, 45% AIM-V medium (Gibco-BRL, Gaithersburg, Md.), 10% FCS, 100 U/ml interleukin-2 (IL-2), and a 0.1 mM solution of MEM non-essential amino acids (Gibco-BRL). A half of the cultured medium was removed every 3 days and replaced with fresh culture medium containing the corresponding peptide (10 μg/ml). On day 15 after culturing, a half of the cultured cells was mixed with T2, C1R-A24, -A26, -A11, C1R-A31, or C1R-A33 cells pulsed with the corresponding peptide and the other half was mixed with T2, C1R-A24, -A26, -A11, C1R-A31, or C1R-A33 cells pulsed with the corresponding control peptide. The respective mixed cultures were incubated for another 18 hours. After that, the supernatants were collected and the level of interferon (IFN)-γ in the supernatants was measured by enzyme-linked immunosorbent assay (ELISA). The induction of peptide-reactive CTLs was decided to be positive when the P value was less than 0.05 and IFN-γ of more than 50 pg/ml was produced in response to cells pulsed with the corresponding peptide, as compared to cells pulsed with the respective control peptides.

Measurement of Cytotoxic Activity

The cytotoxic activity of peptide-stimulated PBMCs against an HLA-A11 positive cell line TSU-PR and an HLA-A11 negative cell line PC93 was measured by a standard 6-hour $^{51}$Cr release assay. As negative control cells were used phytohemagglutinin (PHA)-activated T cells derived from an HLA-A11 positive healthy donor. In round-bottom 96-well plates, $^{51}$Cr-labeled target cells of 2,000 cells per well were cultured with effector cells at indicated ratios of effector cells to target cells. As effector cells were used cells obtained by isolating, immediately prior to experiment for measuring the cytotoxic activity, CD8 positive T cells from peptide-stimulated PBMCs using CD8 Positive Isolation Kit (Dynal, Oslo, Norway). Specific $^{51}$Cr-release was calculated by subtracting the c.p.m. of spontaneous release from the c.p.m. obtained in the experiment. The spontaneous release was determined from the supernatant of a sample which was incubated without effector cells, and subsequently the sample was incubated with 1% Triton X (Wako Pure Chemical Industries, Osaka, Japan) to determine the total release.

Test of Binding of Peptides to HLA-A26 Molecule

RMA-S cells transfected with the HLA-A2601 gene (RMA-S-A2601) were cultured at 26° C. for 20 hours, followed by culturing with each peptide at concentrations of 0.1 to 100 μM and human β2-microglobulin at 26° C. for 2 hours, and then at 37° C. for another 3 hours. After the cells were washed with PBS, the cells were added with an anti-human MHC class-I antibody or HLA-type-specific antibody of an optimal concentration and left in ice for 30 minutes. The cells were washed twice with PBS, and then Alexa Fluor 488 labeled goat anti-mouse IgG was added and allowed to stand in ice for 30 minutes. Measurements were made using a flow cytometer and fluorescence intensities were compared.

Examination of Whether the Peptides are Capable of Inducing HLA-restricted CTLs for Plural HLA Types From candidate peptides for cancer peptide vaccines already identified in the past, peptides binding to HLA-A2, -A24, and -A3 supertype were selected in a total of 34 peptides (9, 13, and 10 peptides, respectively) and examined for the ability to induce HLA-restricted CTLs for HLAs different in the type from the HLA to which each peptide had originally been demonstrated to bind. Peripheral bloods from patients having different HLA types were stimulated with the respective peptides and measured for the ability to induce CTLs by using, as a target, cells pulsed with the peptide corresponding to a C1R transfectant generated by transferring an HLA gene for each type.

Cross reactivity was first examined with the peptides of SEQ ID NO: 1 to SEQ ID NO: 8 among the HLA-A24 binding peptides. EGFR-800 (SEQ ID NO: 1), Lck-488 (SEQ ID NO: 3), SART2-93 (SEQ ID NO: 7), and SART3-109 (SEQ ID NO: 8) induced HLA-restricted CTLs for HLA-A11, to HLA-A2, to HLA-A2 and -A11, and to HLA-A2, -A11, and -A31, respectively (Table 2). In the table, the figures represent the level of IFN-γ (ng/ml), with levels equal to or higher than 50 ng/ml being considered to be significant. Blank entries indicate that the experiment was not carried out and the minus sign (−) means that IFN-γ was at levels below the detection limit.

TABLE 2

Ability of HLA-A24 binding peptides to induce HLA-
restricted CTLs for HLA-A2, HLA-A11, HLA-A31, or HLA-A33

| A24 Patient | | HLA Type | Target | EGFR-800 | Lck-208 | Lck-488 | MAP-1293 | PAP-213 | PSA-248 | SART2-93 | SART3-109 |
|---|---|---|---|---|---|---|---|---|---|---|---|
| A2 | PT | A2/A31 | T2 | 49 | — | 81 | 25 | 17 | 3 | 53 | 234 |
|  | PT | A2/A3 | T2 |  |  |  |  |  |  |  | 19 |
|  | PT | A2/A24 | T2 |  |  |  |  |  |  |  | 57 |
|  | PT | A2 | T2 |  |  |  |  |  |  |  | — |
|  | HD | A2/A24 | T2 |  |  |  |  |  |  |  | — |
|  | HD | A2/A11 | T2 |  |  |  |  |  |  |  | 644 |
| A11 | PT | A11/A33 | C1R-A11 | 183 | 5 | 13 | — | — | — | 238 | — |
|  | PT | A11 | C1R-A11 |  |  |  |  |  |  |  | 265 |
|  | PT | A11 | C1R-A11 |  |  |  |  |  |  |  | 17 |
|  | PT | A11 | C1R-A11 |  |  |  |  |  |  |  | — |
|  | PT | A11/A2 | C1R-A11 |  |  |  |  |  |  |  | 376 |
|  | HD | A2/A11 | C1R-A11 |  |  |  |  |  |  |  | 202 |
|  | HD | A11/A24 | C1R-A11 |  |  |  |  |  |  |  | — |
|  | HD | A11/A11 | C1R-A11 |  |  |  |  |  |  |  | 650 |
| A31 | PT | A2/A31 | C1R-A31 | — | — | — | — | 15 | 17 | — | 26 |
|  | PT | A2/A31 | C1R-A31 |  |  |  |  |  |  |  | 49 |
|  | HD | A31/A33 | C1R-A31 |  |  |  |  |  |  |  | 67 |
| A33 | PT | A11/A33 | C1R-A33 | — | — | 17 | 40 | — | — | — | — |
|  | HD | A31/A33 | C1R-A33 |  |  |  |  |  |  |  | 29 |

Similarly, cross reactivity was examined with the peptides of SEQ ID NO: 9 to SEQ ID NO: 16 among the HLA-A2 binding peptides. CypB-128 (SEQ ID NO: 15), Lck-246 (SEQ ID NO: 10), Lck-422 (SEQ ID NO: 16), ppMAPkkk (SEQ ID NO: 11), WHSC2-103 (SEQ ID NO: 12), UBE-43 (SEQ ID NO: 13), and HNRPL-501 (SEQ ID NO: 14) were found to be capable of inducing HLA-restricted CTLs for HLA-A24, to HLA-A11 and -31, to HLA-A31, to HLA-11 and HLA-A31, to HLA-A24 and -A31, to HLA-A24 and -A31, and to HLA-A24 and -A11, respectively (Table 3). In the table, the figures represent the level of IFN-γ (ng/ml), with levels equal to or higher than 50 ng/ml being considered to be significant.

TABLE 3

Ability of HLA-A2 binding peptides to induce
HLA-restricted CTLs for HLA-A24, HLA-A11, or HLA-A31

| A2 Peptides Patient | | HLA Type | Target | SART3-302 | CypB-129 | Lck-246 | Lck-422 | MAP-432 | WHSC2-103 | UBE-43 | HNRPL-501 |
|---|---|---|---|---|---|---|---|---|---|---|---|
| A24 | PT | A24/A31 | C1R-A24 | — | 32 | — | 13 | — | — | — | — |
|  | PT | A24/A31 | C1R-A24 | — | 12 | 11 | 10 | 15 | — | 85 | 9 |
|  | PT | A24/A31 | C1R-A24 | — | — | 17 | 28 | 4 | 91 | 50 | 60 |
|  | PT |  | C1R-A24 | — | 86 | 29 | — | 6 | — | — | — |
| A11 | PT | A11/A31 | C1R-A11 | 0 | 0 | 146 | 0 | 0 | 0 | 0 | 3 |
|  | PT | A11/A24 | C1R-A11 | — | — | 6 | — | 44 | — | — | 130 |
| A31 | PT |  | C1R-A31 | — | 9 | 48 | 21 | 138 | — | 73 | 35 |
|  | PT | A24/A31 | C1R-A31 | 0 | 0 | 25 | 0 | 0 | 0 | 0 | 0 |
|  | PT | A24/A31 | C1R-A31 | 20 | 32 | 115 | 474 | 14 | 55 | 32 | — |

In addition, cross reactivity was examined with the peptides of SEQ ID NO: 17 to SEQ ID NO: 27 among the HLA-A3 supertype binding peptides. β-tubulin5-154 (SEQ ID NO: 18), Lck-90 (SEQ ID NO: 19), IEX1-47 (SEQ ID NO: 22), and SART3-511 (SEQ ID NO: 23) were found to be capable of inducing HLA-restricted CTLs for A24, A2, A24, and A2, respectively (Table 4). In the table, the figures represent the level of IFN-γ (ng/ml), with levels equal to or higher than 50 ng/ml being considered to be significant.

TABLE 4

Ability of HLA-A3 binding peptides to induce HLA-restricted CTLs for HLA-A2 or HLA-A24

| Patient | HLA Type | Target | SART3 511 | SART3 734 | Lck 90 | Lck 449 | PAP 248 | PSA 16 | IEX1 47 | βt5 154 |
|---|---|---|---|---|---|---|---|---|---|---|
| A2 |
| 1 | PT A2/A24 | T2 | 90 | 30 | 1341 | — | — | — | — | — |
| A24 |
| 1 | PT A24 | C1R-A24 | — | — | — | — | — | — | 102 | 128 |
| 2 | PT A24 | C1R-A24 | — | — | 40 | — | — | — | — | — |
| 3 | PT A24 | C1R-A24 | 6 | 44 | 7 | — | — | 4 | — | 10 |
| 4 | PT A24 | C1R-A24 | — | — | — | — | — | — | — | — |
| 5 | PT A24 | C1R-A24 | — | — | — | — | — | — | — | 32 |
| 6 | PT A24 | C1R-A24 | 25 | 12 | — | 17 | — | 27 | 522 | — |
| 7 | PT A2/A24 | C1R-A24 | 11 | 9 | — | 41 | 4 | 40 | 14 | — |

Different HLA-A3-Supertype-Restricted Cytotoxic Activity

SART3-109 (SEQ ID NO: 8), a peptide known to bind to HLA-24, was used to stimulate PBMCs from a HLA-A11 positive prostate cancer patient to induce CTLs. The cytotoxic activity of the resulting CTLs was ascertained in chromium release reaction. As to the cytotoxic activity against an HLA-A11 positive cell line, TSU-PR, the rate of chromium release was shown to be significantly high against the cell line relative to an HLA-A11 negative cell line, PC93, and PHA stimulated lymphoblasts from HLA-A11 positive healthy donors (FIG. 1).

Test of Binding of Peptides to HLA-A26

Figure 2:
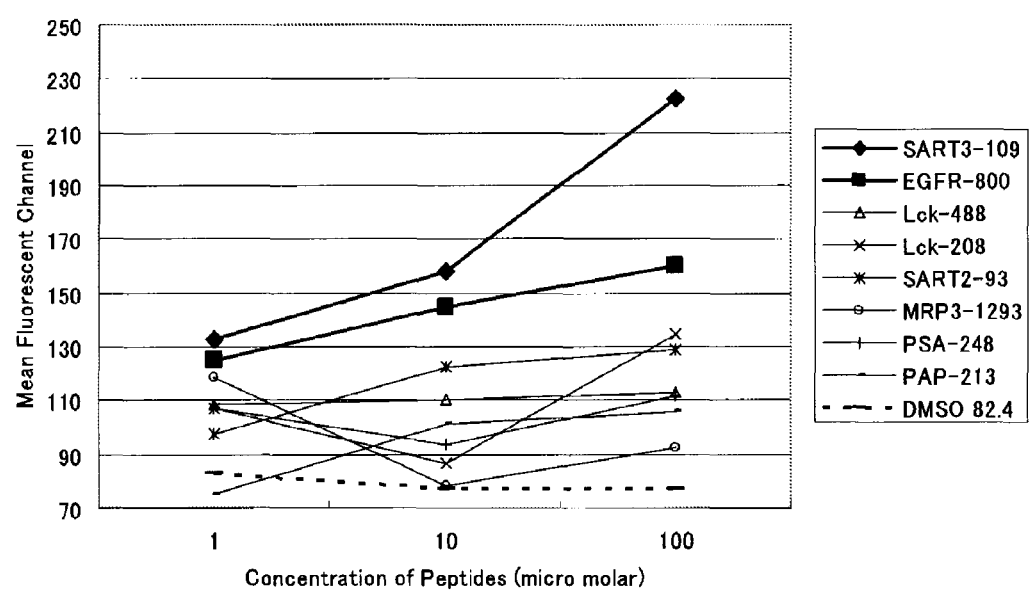
FIG. 2 shows binding activity of different peptides having different binding properties to bind to HLA-A26 positive cells.
Figure 3:
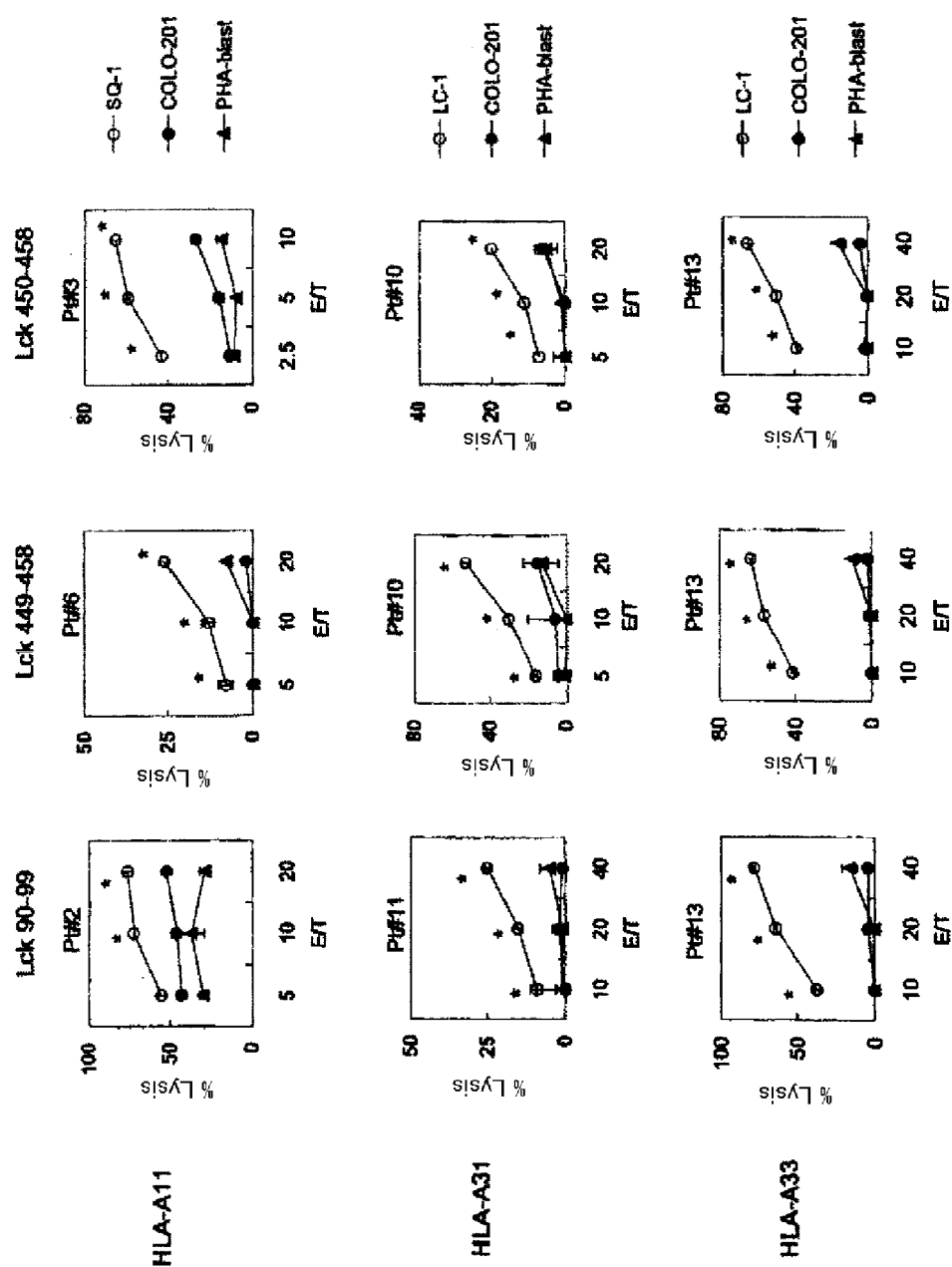
FIG. 3 shows cytotoxic activities of peptide-stimulated PBMCs from HLA-A3 supertype allele-positive prostate cancer patients. PBMCs from HLA-A3 supertype allele-positive prostate cancer patients were stimulated with peptides and cytotoxic activities of the PBMCs against plural target cells were measured by 6-hour $^{51}$Cr release assay. As control was used PHA-stimulated, blast-forming T-cell blasts from HLA-A3 supertype allele-positive healthy volunteers. *$p<0.05$.

The ability of various peptides to bind to RMA-S-A2601 was examined. The peptides were dissolved in DMSO and used. DMSO alone was used as a negative control. From the results of these experiments, SART3-109 (SEQ ID NO: 8) capable of inducing HLA-A24-restricted CTLs was revealed to bind also to HLA-A26, which belongs to a completely different HLA supertype. Also, it was suggested that EGFR-800 (SEQ ID NO: 1), which is similarly restricted to HLA-A24, also binds, albeit at weak levels, to an HLA-A26 molecule (FIG. 2).

Ability of Lck-90 and Lck-449 Peptides to Bind to HLA-A3 Supertype Alleles

The data indicating the ability of Lck-90 (SEQ ID NO: 19) and Lck-449 (SEQ ID NO: 17) peptides to bind to HLA-A3 supertype alleles as disclosed in Patent Document 9 is as follows.

It was ascertained that for Lck-90 and Lck-449 peptides, peptide-reactive IgGs were observed highly frequently in the plasmas of HLA-A3 positive prostate cancer patients. Also, the ability to induce Lck-90 and Lck-449 peptide-specific CTLs from PBMCs derived from HLA-A3 supertype allele positive prostate cancer patients was ascertained by the above-described method. Lck-90 and Lck-449 peptides induced CTLs reactive with the corresponding peptides, from the PBMCs derived from five and two patients in seven HLA-A11 positive cancer patients, from three and three patients in five HLA-A31 positive cancer patients, and from two and three patients in five HLA-A33 positive cancer patients, respectively.

PBMCs from HLA-A3 supertype allele positive prostate cancer patients were stimulated in vitro with Lck-90 (SEQ ID NO: 19) or Lck-449 (SEQ ID NO: 17) peptide to examine whether the peptide-reactive CTLs thus induced displayed cytotoxic activity against cancer cells. PBMCs derived from HLA-A11 positive patients which were stimulated with each of Lck-90 and Lck-449 peptides exhibited higher levels of cytotoxic activity against HLA-A11 positive SQ-1 cells than against HLA-A11 negative COLO 201 cells and the negative control, PHA stimulated, blast-forming T-cell blasts derived from HLA-A11 positive healthy donors.

Similarly, these peptides were found to be capable of inducing LC-1 (HLA-A31$^+$/-A33$^+$)-reactive CTLs from the PBMCs derived from HLA-A31 positive patients and HLA-A33 positive patients. The CTLs specific for each peptide exhibited a stronger cytotoxic activity against LC-1 cells than against COLO 201 cells or blast-forming T-cells. Therefore, it was shown that PBMCs stimulated in vitro with Lck-90 and Lck-449 peptides exerted cytotoxic activity against cancer cells in HLA-A11, -A31, and -A33-restricted manners.

Measurement of Cytotoxic Activity

PBMCs derived from cancer patients with various HLA types were stimulated with peptides to examine the activity of the peptides to induce CTLs against each of the HLA types. As target cells were used cancer cell lines each having an HLA type corresponding to the HLA type of each patient and cytotoxic activity against the target cells were measured by a standard 6-hour $^{51}$Cr release assay.

The target cells which were used in this measurement were the following cancer cell lines: PC93 (A68), KE4 (A24/A26), KE5 (A1101/), PC93-A24 (A24/A68), PC93-A33 (A33/A68), PC93-A31 (A31/A68), COLO 201 (A0101/0201), 11-18 (A0201/A2402), TSU-PR (A11), LC-1 (A3101/A3303), Panc-1 (A0201/A1101), LC-1 (A3101/A3303), LC65A (1101/2402), LNCap-A11 (A11/A0101/0201), KNS42 (A2402/2601), LNCap-A24 (A24/A0101/0201), and LNCap-A31 (A31/A0101/0201). As negative controls were used QG56 (A2601), PC93 (A68), LNCap (A0101/0201), LC-1 (A3101/A3303), COLO 201 (A0101/0201), COLO 320 (A2402/), and K562. The HLA type of each of the cell lines is indicated in parentheses. In connection with the above, it is meant that PC93(WT) expresses HLA-A68, and for example, when a target cell is represented as PC93-A24, it is a stable transfectant generated by introducing a gene coding for HLA-A24. All the tumor cell lines were cultured in RPMI 1640 containing 10% FCS (Invitrogen). In Table 5 indicating the results, HLA is described only for transfectants and "(WT)" is described for non-transfectants.

In Table 5 indicating the results, "+" was marked by examining the cytotoxic activity mediated by peptide-activated PBMCs, in a similar way using, as negative control target cells, tumor cell lines having a different HLA type from the HLA type of a cancer patient from whom the PBMCs were derived, and when a statistically significant cytotoxic activity against HLA-matched target cells was found relative to the cytotoxic activity against the negative control target cells, it was recognized that the induction of HLA-restricted cytotoxic activity for said HLA type had been taken place. Table 5 describes the HLA-matched target cells and control target cells which were used in the test. When such cells are not described in the table and "+" is given, it means that the activity of the peptide for inducing HLA-restricted CTLs for the HLA type indicated is already known.

For peptide-specific CTL activities of C35-44 (SEQ ID NO: 25), which is an HCV-derived peptide, its activities were measured in chromium release reaction according to a routine procedure employing cells obtained by stimulating PBMCs derived from HCV-infected patients with the C35-55 peptide, and using C1R cells transfected with each of the corresponding HLA genes stably and pulsed with C35-44 as HLA-matched target cells, and C1R(WT) as negative control target cells.

In round-bottom 96-well plates, $^{51}$Cr-labeled target cells of 2,000 cells per well were cultured with effector cells at an effector-cell-to-target-cell ratio of 40. As effector cells were used cells obtained by isolating, immediately prior to experiment for measuring the cytotoxic activity, CD8 positive T cells from peptide-activated PBMCs using CD8 Positive Isolation Kit (Dynal, Oslo, Norway). Specific $^{51}$Cr-release was calculated by subtracting the c.p.m. of spontaneous release from the c.p.m. obtained in the experiment. The spontaneous release was determined from the supernatant of a sample which was incubated without effector cells, and subsequently the sample was incubated with 1% Triton X (Wako Pure Chemical Industries, Osaka, Japan) to determine the total release.

The HLA type and peptide specificity of the induced HLA-restricted CTLs were identified in a specific suppression experiment using monoclonal antibodies directed against HLA class-I and CD8 and in a cold-target suppression experiment using unlabeled target cells, respectively. These experiments were carried out in triplicate, and considered to be positive and indicated with +, when the suppression was observed with the antibodies or the cold target (target cells which were not labeled with the isotope) at significant levels (P<0.05), as compared to the negative control.

Results

HLA-A2 Binding Peptides

It was demonstrated that C35-44 (SEQ ID NO: 25) had the ability to induce HLA-restricted CTLs for HLA-A2402, A2601, A3101, A3303, and A1101.

It was demonstrated that CypB-129 (SEQ ID NO: 15), Lck-422 (SEQ ID NO: 16), SART3-302 (SEQ ID NO: 9), UBE-43 (SEQ ID NO: 13), and WHSC2-103 (SEQ ID NO: 13) had the ability to induce HLA-restricted CTLs for HLA-A3101.

It was demonstrated that HNRPL-501 (SEQ ID NO: 14) and ppMAPkkk-432 (SEQ ID NO: 11) had the ability to induce HLA-restricted CTLs for HLA-2601.

HLA-A24 Binding Peptides

It was confirmed that SART3-109 (SEQ ID NO:), Lck208, EGRF-800, and SART2-93 had the ability to induce HLA-restricted CTLs for HLA-A3101, A3303, and A1101, for HLA-A1101, for HLA-A0201, and for HLA-A0201 and A0207, respectively.

HLA-A3 Binding Peptides

PAP-155, β-tubline-309, and Lck-90 were shown to have the ability to induce HLA-restricted CTLs for HLA-A0201 and -A2402, and for HLA-A2402, respectively. These results are summarized in Table 5.

TABLE 5

| Peptide Name Target Cell | Sequence SEQ ID NO: | Known HLA-Restriction | HLA-A2 A0201 | HLA-A24 A2402 |
|---|---|---|---|---|
| C35-44 | YLLPRRGPRL | A2 | + | + |
| HLA-Matched Target Cell | 25 | | | C1R-A24 |
| Control Target Cell | | | | C1R(WT) |
| SART3-109 | VYDYNCHVDL | A24 | − | + |
| HLA-Matched Target Cell | 8 | | | COLO201(WT) |
| Control Target Cell | | | | PC93(WT) |
| Lck-208 | HYTNASDGL | A24 | − | + |
| HLA-Matched Target Cell | 2 | | | COLO201(WT) |
| Control Target Cell | | | | LC-1(WT) |
| EGFR-800 | DYVREHKDNI | A24 | + | + |
| HLA-Matched Target Cell | 1 | | | 11-18(WT) |

TABLE 5-continued

| Peptide Name | Sequence | HLA | | |
|---|---|---|---|---|
| Control Target Cell | | | | LNCap(WT) |
| SART2-93 | DYSARWNEI 7 | A24 | + | + |
| HLA-Matched Target Cell | | | Panc-1(WT) | |
| Control Target Cell | | | | LNCap(WT) |
| CypB-129 | KLKHYGPGWV 15 | A2 | + | − |
| HLA-Matched Target Cell | | | | PC93-A24 |
| Control Target Cell | | | | PC93(WT) |
| Lck-422 | DVWSFGILL 16 | A2 | + | − |
| HLA-Matched Target Cell | | | | PC93-A24 |
| Control Target Cell | | | | PC93(WT) |
| SART3-302 | LLQAEAPRL 9 | A2 | + | − |
| HLA-Matched Target Cell | | | | PC93-A24 |
| Control Target Cell | | | | PC93(WT) |
| UBE-43 | RLQEWCSVI 13 | A2 | + | − |
| HLA-Matched Target Cell | | | | LNCap-A24 |
| Control Target Cell | | | | LNCap(WT) |
| WHSC2-103 | ASLDSDPWV 12 | A2 | + | − |
| HLA-Matched Target Cell | | | | LNCap-A24 |
| Control Target Cell | | | | LNCap(WT) |
| HNRPL501 | NVLHFFNAPL 14 | A2 | + | nd |
| HLA-Matched Target Cell | | | | |
| Control Target Cell | | | | |
| ppMAPkkk-432 | DLLSHAFFA 11 | A2 | + | nd |
| HLA-Matched Target Cell | | | | |
| Control Target Cell | | | | |
| PAP-155 | YLPFRNCPR 26 | A3 | + | + |
| HLA-Matched Target Cell | | | COLO201(WT) | PC93(WT) |
| Control Target Cell | | | COLO320(WT) | LNCap(WT) |
| β-tubline-309 | KIREEYPDR 27 | A3 | nd | + |
| HLA-Matched Target Cell | | | | PC93(WT) |
| Control Target Cell | | | | LNCap(WT) |
| Lck-90 | ILEQSGEWWK 19 | A3 | nd | + |
| HLA-Matched Target Cell | | | | KE4(WT) |
| Control Target Cell | | | | COLO201(WT) |

| Peptide Name | HLA-A26 | HKA-A3 supertype | | |
|---|---|---|---|---|
| Target Cell | A2601 | A3101 | A3303 | A1101 |
| C35-44 | + | + | + | + |
| HLA-Matched Target Cell | C1R-A26 | C1R-A31 | C1R-A33 | C1R-A11 |

TABLE 5-continued

| Control Target Cell | C1R(WT) | C1R(WT) | C1R(WT) | C1R(WT) |
|---|---|---|---|---|
| SART3-109 | nd | + | + | + |
| HLA-Matched Target Cell | | LC-1(WT) | LC-1(WT) | TSU-PR(WT) |
| Control Target Cell | | PC93(WT) | PC93(WT) | PC93(WT) |
| Lck-208 | nd | nd | nd | + |
| HLA-Matched Target Cell | | | | TSU-PR(WT) |
| Control Target Cell | | | | PC93(WT) |
| EGFR-800 | nd | nd | − | − |
| HLA-Matched Target Cell | | | PC93-A33 | LC65A(WT) |
| Control Target Cell | | | PC93(WT) | QG56(WT) |
| SART2-93 | nd | nd | − | − |
| HLA-Matched Target Cell | | | | LNCap-A11 |
| Control Target Cell | | | | LNCap(WT) |
| CypB-129 | nd | + | nd | nd |
| HLA-Matched Target Cell | | PC93-A31 | | |
| Control Target Cell | | PC93(WT) | | |
| Lck-422 | nd | + | nd | − |
| HLA-Matched Target Cell | | LC-1(WT) | | TSU-PR(WT) |
| Control Target Cell | | PC93(WT) | | PC93(WT) |
| SART3-302 | nd | + | nd | − |
| HLA-Matched Target Cell | | LC-1(WT) | | KE5(WT) |
| Control Target Cell | | PC93(WT) | | PC93(WT) |
| UBE-43 | nd | + | nd | − |
| HLA-Matched Target Cell | | LNCap-A31 | | TSU-PR(WT) |
| Control Target Cell | | LNCap(WT) | | LNCap(WT) |
| WHSC2-103 | nd | + | nd | nd |
| HLA-Matched Target Cell | | LC-1(WT) | | |
| Control Target Cell | | PC-93(WT) | | |
| HNRPL501 | + | nd | nd | nd |
| HLA-Matched Target Cell | KNS42(WT) | | | |
| Control Target Cell | Panc1 | | | |
| ppMAPkkk-432 | + | nd | nd | nd |
| HLA-Matched Target Cell | KNS42(WT) | | | |
| Control Target Cell | Panc-1 | | | |
| PAP-155 | nd | + | + | + |
| HLA-Matched Target Cell | | | | |
| Control Target Cell | | | | |
| β-tubline-309 | nd | + | + | + |
| HLA-Matched Target Cell | | | | |

TABLE 5-continued

| | | | | |
|---|---|---|---|---|
| Control Target Cell | | | | |
| Lck-90 | nd | + | + | + |
| HLA-Matched Target Cell | | | | |
| Control Target Cell | | | | |

+ CTL induction
− No CTL induction
nd Not done

As can be understood from the results described above, the peptides of SEQ ID NOS: 1 to 27 as specified in the present invention can induce HLA-specific CTLs in patients of two or more patient groups selected from the group consisting of an HLA-A2 positive patient group, an HLA-A24 positive patient group, an HLA-A26 positive patient group, and an HLA-A3 supertype positive patient group, and thus are suitably used for the treatment or prevention of such patients. The peptides of SEQ ID NOS: 1 to 24 and SEQ ID NOS: 26 to 27 of the present invention are particularly suitably used as an active ingredient of cancer peptide vaccine and the peptide of SEQ ID NO: 25 of the present invention is suitably used for the treatment or prevention of diseases related to hepatitis C virus.

The invention claimed is:

1. A method for the treatment of cancer in an HLA-A3 supertype positive patient, which comprises administering a cytotoxic T lymphocyte inducer composition which comprises one or more peptides selected from the group consisting of SART3-302 (SEQ ID NO: 9), Lck-246 (SEQ ID NO: 10), ppMAPkkk-432 (SEQ ID NO: 11), and HNRPL-501 (SEQ ID NO: 14) to an HLA-A3 supertype positive patient.

2. The method of claim 1, wherein the HLA-A3 supertype is HLA-A11 or HLA-A31.

3. The method of claim 1, wherein the administration of the cytotoxic T lymphocyte inducer composition comprises intradermal administration or subcutaneous administration.

4. The method of claim 1, wherein the one or more peptides are administered in an amount of 0.1 to 5 mg.

5. A method for the treatment of cancer in an HLA-A26 positive patient, which comprises administering a cytotoxic T lymphocyte inducer composition which comprises one or more peptides selected from the group consisting of ppMAPkkk-432 (SEQ ID NO: 11) and HNRPL-501 (SEQ ID NO: 14) to an HLA-A26 positive patient.

6. The method of claim 5, wherein the administration of the cytotoxic T lymphocyte inducer composition comprises intradermal administration or subcutaneous administration.

7. The method of claim 5, wherein the one or more peptides are administered in an amount of 0.1 to 5 mg.

8. A method for the treatment of cancer in an HLA-A24 positive patient, which comprises administering a cytotoxic T lymphocyte inducer composition which comprises HNRPL-501 (SEQ ID NO: 14) to an HLA-A24 positive patient.

9. The method of claim 8, wherein the administration of the cytotoxic T lymphocyte inducer composition comprises intradermal administration or subcutaneous administration.

10. The method of claim 8, wherein the one or more peptides are administered in an amount of 0.1 to 5 mg.

* * * * *

SEQUENCE LISTING

```
<160> NUMBER OF SEQ ID NOS: 38

<210> SEQ ID NO 1
<211> LENGTH: 10
<212> TYPE: PRT
<213> ORGANISM: Artificial sequence
<220> FEATURE:
<223> OTHER INFORMATION: Synthetic construct; EGFR-800 peptide

<400> SEQUENCE: 1

Asp Tyr Val Arg Glu His Lys Asp Asn Ile
1               5                   10

<210> SEQ ID NO 2
<211> LENGTH: 9
<212> TYPE: PRT
<213> ORGANISM: Artificial sequence
<220> FEATURE:
<223> OTHER INFORMATION: Synthetic construct; Lck-208 peptide

<400> SEQUENCE: 2

His Tyr Thr Asn Ala Ser Asp Gly Leu
1               5

<210> SEQ ID NO 3
<211> LENGTH: 10
<212> TYPE: PRT
<213> ORGANISM: Artificial sequence
<220> FEATURE:
<223> OTHER INFORMATION: Synthetic construct; Lck-488 peptide

<400> SEQUENCE: 3

Asp Tyr Leu Arg Ser Val Leu Glu Asp Phe
1               5                   10

<210> SEQ ID NO 4
<211> LENGTH: 10
<212> TYPE: PRT
<213> ORGANISM: Artificial sequence
<220> FEATURE:
<223> OTHER INFORMATION: Synthetic construct; MRP3-1293 peptide

<400> SEQUENCE: 4

Asn Tyr Ser Val Arg Tyr Arg Pro Gly Leu
1               5                   10
```

```
<210> SEQ ID NO 5
<211> LENGTH: 9
<212> TYPE: PRT
<213> ORGANISM: Artificial sequence
<220> FEATURE:
<223> OTHER INFORMATION: Synthetic construct; PAP-213 peptide

<400> SEQUENCE: 5

Leu Tyr Cys Glu Ser Val His Asn Phe
1               5

<210> SEQ ID NO 6
<211> LENGTH: 10
<212> TYPE: PRT
<213> ORGANISM: Artificial sequence
<220> FEATURE:
<223> OTHER INFORMATION: Synthetic construct; PSA-248 peptide

<400> SEQUENCE: 6

His Tyr Arg Lys Trp Ile Lys Asp Thr Ile
1               5                   10

<210> SEQ ID NO 7
<211> LENGTH: 9
<212> TYPE: PRT
<213> ORGANISM: Artificial sequence
<220> FEATURE:
<223> OTHER INFORMATION: Synthetic construct; SART2-93 peptide

<400> SEQUENCE: 7

Asp Tyr Ser Ala Arg Trp Asn Glu Ile
1               5

<210> SEQ ID NO 8
<211> LENGTH: 10
<212> TYPE: PRT
<213> ORGANISM: Artificial sequence
<220> FEATURE:
<223> OTHER INFORMATION: Synthetic construct; SART3-109 peptide

<400> SEQUENCE: 8

Val Tyr Asp Tyr Asn Cys His Val Asp Leu
1               5                   10

<210> SEQ ID NO 9
<211> LENGTH: 9
<212> TYPE: PRT
<213> ORGANISM: Artificial sequence
<220> FEATURE:
<223> OTHER INFORMATION: Synthetic construct; SART3-302 peptide

<400> SEQUENCE: 9

Leu Leu Gln Ala Glu Ala Pro Arg Leu
1               5

<210> SEQ ID NO 10
<211> LENGTH: 9
<212> TYPE: PRT
<213> ORGANISM: Artificial sequence
<220> FEATURE:
<223> OTHER INFORMATION: Synthetic construct; Lck-246 peptide

<400> SEQUENCE: 10

Lys Leu Val Glu Arg Leu Gly Ala Ala
1               5
```

<210> SEQ ID NO 11
<211> LENGTH: 9
<212> TYPE: PRT
<213> ORGANISM: Artificial sequence
<220> FEATURE:
<223> OTHER INFORMATION: Synthetic construct; ppMAPkkk-432 peptide

<400> SEQUENCE: 11

Asp Leu Leu Ser His Ala Phe Phe Ala
1               5

<210> SEQ ID NO 12
<211> LENGTH: 9
<212> TYPE: PRT
<213> ORGANISM: Artificial sequence
<220> FEATURE:
<223> OTHER INFORMATION: Synthetic construct; WHSC2-103 peptide

<400> SEQUENCE: 12

Ala Ser Leu Asp Ser Asp Pro Trp Val
1               5

<210> SEQ ID NO 13
<211> LENGTH: 9
<212> TYPE: PRT
<213> ORGANISM: Artificial sequence
<220> FEATURE:
<223> OTHER INFORMATION: Synthetic construct; UBE-43 peptide

<400> SEQUENCE: 13

Arg Leu Gln Glu Trp Cys Ser Val Ile
1               5

<210> SEQ ID NO 14
<211> LENGTH: 10
<212> TYPE: PRT
<213> ORGANISM: Artificial sequence
<220> FEATURE:
<223> OTHER INFORMATION: Synthetic construct; HNRPL-501 peptide

<400> SEQUENCE: 14

Asn Val Leu His Phe Phe Asn Ala Pro Leu
1               5                   10

<210> SEQ ID NO 15
<211> LENGTH: 10
<212> TYPE: PRT
<213> ORGANISM: Artificial sequence
<220> FEATURE:
<223> OTHER INFORMATION: Synthetic construct; CypB-129 peptide

<400> SEQUENCE: 15

Lys Leu Lys His Tyr Gly Pro Gly Trp Val
1               5                   10

<210> SEQ ID NO 16
<211> LENGTH: 9
<212> TYPE: PRT
<213> ORGANISM: Artificial sequence
<220> FEATURE:
<223> OTHER INFORMATION: Synthetic construct; Lck-422 peptide

<400> SEQUENCE: 16

Asp Val Trp Ser Phe Gly Ile Leu Leu
1               5

<210> SEQ ID NO 17
<211> LENGTH: 10
<212> TYPE: PRT
<213> ORGANISM: Artificial sequence
<220> FEATURE:
<223> OTHER INFORMATION: Synthetic construct; Lck-449 peptide

<400> SEQUENCE: 17

Val Ile Gln Asn Leu Glu Arg Gly Tyr Arg
1               5                   10

<210> SEQ ID NO 18
<211> LENGTH: 9
<212> TYPE: PRT
<213> ORGANISM: Artificial sequence
<220> FEATURE:
<223> OTHER INFORMATION: Synthetic construct; beta-tubulin 5-154 peptide

<400> SEQUENCE: 18

Lys Ile Arg Glu Glu Tyr Pro Asp Arg
1               5

<210> SEQ ID NO 19
<211> LENGTH: 10
<212> TYPE: PRT
<213> ORGANISM: Artificial sequence
<220> FEATURE:
<223> OTHER INFORMATION: Synthetic construct; Lck-90 peptide

<400> SEQUENCE: 19

Ile Leu Glu Gln Ser Gly Glu Trp Trp Lys
1               5                   10

<210> SEQ ID NO 20
<211> LENGTH: 9
<212> TYPE: PRT
<213> ORGANISM: Artificial sequence
<220> FEATURE:
<223> OTHER INFORMATION: Synthetic construct; PSA-16 peptide

<400> SEQUENCE: 20

Gly Ala Ala Pro Leu Ile Leu Ser Arg
1               5

<210> SEQ ID NO 21
<211> LENGTH: 10
<212> TYPE: PRT
<213> ORGANISM: Artificial sequence
<220> FEATURE:
<223> OTHER INFORMATION: Synthetic construct; PAP-248 peptide

<400> SEQUENCE: 21

Gly Ile His Lys Gln Lys Glu Lys Ser Arg
1               5                   10

<210> SEQ ID NO 22
<211> LENGTH: 10
<212> TYPE: PRT
<213> ORGANISM: Artificial sequence
<220> FEATURE:
<223> OTHER INFORMATION: Synthetic construct; IEX1-47 peptide

<400> SEQUENCE: 22

Ala Pro Ala Gly Arg Pro Ser Ala Ser Arg
1               5                   10

<210> SEQ ID NO 23

```
<211> LENGTH: 9
<212> TYPE: PRT
<213> ORGANISM: Artificial sequence
<220> FEATURE:
<223> OTHER INFORMATION: Synthetic construct; SART3-511 peptide

<400> SEQUENCE: 23

Trp Leu Glu Tyr Tyr Asn Leu Glu Arg
1               5

<210> SEQ ID NO 24
<211> LENGTH: 9
<212> TYPE: PRT
<213> ORGANISM: Artificial sequence
<220> FEATURE:
<223> OTHER INFORMATION: Synthetic construct; SART3-734 peptide

<400> SEQUENCE: 24

Gln Ile Arg Pro Ile Phe Ser Asn Arg
1               5

<210> SEQ ID NO 25
<211> LENGTH: 10
<212> TYPE: PRT
<213> ORGANISM: Artificial sequence
<220> FEATURE:
<223> OTHER INFORMATION: Synthetic construct; C35-44 peptide

<400> SEQUENCE: 25

Tyr Leu Leu Pro Arg Arg Gly Pro Arg Leu
1               5                   10

<210> SEQ ID NO 26
<211> LENGTH: 9
<212> TYPE: PRT
<213> ORGANISM: Artificial sequence
<220> FEATURE:
<223> OTHER INFORMATION: Synthetic construct; PAP-155 protein

<400> SEQUENCE: 26

Tyr Leu Pro Phe Arg Asn Cys Pro Arg
1               5

<210> SEQ ID NO 27
<211> LENGTH: 9
<212> TYPE: PRT
<213> ORGANISM: Artificial sequence
<220> FEATURE:
<223> OTHER INFORMATION: Synthetic construct; Beta-tubline 309 peptide

<400> SEQUENCE: 27

Lys Ile Arg Glu Glu Tyr Pro Asp Arg
1               5

<210> SEQ ID NO 28
<211> LENGTH: 9
<212> TYPE: PRT
<213> ORGANISM: Artificial sequence
<220> FEATURE:
<223> OTHER INFORMATION: Synthetic construct; MRP503 peptide

<400> SEQUENCE: 28

Leu Tyr Ala Trp Glu Pro Ser Phe Leu
1               5

<210> SEQ ID NO 29
<211> LENGTH: 9
```

```
<212> TYPE: PRT
<213> ORGANISM: Artificial sequence
<220> FEATURE:
<223> OTHER INFORMATION: Synthetic construct; PSM624 peptide

<400> SEQUENCE: 29

Thr Tyr Ser Val Ser Phe Asp Ser Leu
1               5

<210> SEQ ID NO 30
<211> LENGTH: 9
<212> TYPE: PRT
<213> ORGANISM: Artificial sequence
<220> FEATURE:
<223> OTHER INFORMATION: Synthetic construct; PAP 213 peptide

<400> SEQUENCE: 30

Leu Tyr Cys Glu Ser Val His Asn Phe
1               5

<210> SEQ ID NO 31
<211> LENGTH: 9
<212> TYPE: PRT
<213> ORGANISM: Artificial sequence
<220> FEATURE:
<223> OTHER INFORMATION: Synthetic construct; SART2 161 peptide

<400> SEQUENCE: 31

Ala Tyr Asp Phe Leu Tyr Asn Tyr Leu
1               5

<210> SEQ ID NO 32
<211> LENGTH: 9
<212> TYPE: PRT
<213> ORGANISM: Artificial sequence
<220> FEATURE:
<223> OTHER INFORMATION: Synthetic construct; Lck 486 peptide

<400> SEQUENCE: 32

Thr Phe Asp Tyr Leu Arg Ser Val Leu
1               5

<210> SEQ ID NO 33
<211> LENGTH: 9
<212> TYPE: PRT
<213> ORGANISM: Artificial sequence
<220> FEATURE:
<223> OTHER INFORMATION: Synthetic construct; LCk 450 peptide

<400> SEQUENCE: 33

Ile Gln Asn Leu Glu Arg Gly Tyr Arg
1               5

<210> SEQ ID NO 34
<211> LENGTH: 9
<212> TYPE: PRT
<213> ORGANISM: Artificial sequence
<220> FEATURE:
<223> OTHER INFORMATION: Synthetic construct; CGI 37 peptide

<400> SEQUENCE: 34

Lys Phe Thr Lys Thr His Lys Phe Arg
1               5

<210> SEQ ID NO 35
<211> LENGTH: 9
<212> TYPE: PRT
```

```
<213> ORGANISM: Artificial sequence
<220> FEATURE:
<223> OTHER INFORMATION: Synthetic construct; Gag 77-85 peptide

<400> SEQUENCE: 35

Ser Leu Tyr Asn Thr Val Ala Thr Leu
1               5

<210> SEQ ID NO 36
<211> LENGTH: 9
<212> TYPE: PRT
<213> ORGANISM: Artificial sequence
<220> FEATURE:
<223> OTHER INFORMATION: Synthetic construct; env-GP peptide

<400> SEQUENCE: 36

Arg Tyr Leu Arg Asp Gln Gln Leu Leu
1               5

<210> SEQ ID NO 37
<211> LENGTH: 9
<212> TYPE: PRT
<213> ORGANISM: Artificial sequence
<220> FEATURE:
<223> OTHER INFORMATION: Synthetic construct; HIV-Gag167-175 peptide

<400> SEQUENCE: 37

Glu Val Ile Pro Met Phe Ser Ala Leu
1               5

<210> SEQ ID NO 38
<211> LENGTH: 11
<212> TYPE: PRT
<213> ORGANISM: Artificial sequence
<220> FEATURE:
<223> OTHER INFORMATION: Synthetic construct; MRP503 peptide

<400> SEQUENCE: 38

Arg Leu Arg Asp Leu Leu Leu Ile Val Thr Arg
1               5                   10
```